US009315551B2

(12) United States Patent
Kwang et al.

(10) Patent No.: US 9,315,551 B2
(45) Date of Patent: Apr. 19, 2016

(54) PORCINE CIRCOVIRUS TYPE 2 VACCINES

(75) Inventors: Hwei-Sing Kwang, Singapore (SG); Isabelle Gek Joo Chen, Singapore (SG); Hui Kheng Chua, Singapore (SG); Jue Liu, Singapore (SG)

(73) Assignee: Temasek Life Sciences Laboratory Ltd., Singapore (SG)

( * ) Notice: Subject to any disclaimer, the term of this patent is extended or adjusted under 35 U.S.C. 154(b) by 889 days.

(21) Appl. No.: 11/920,877

(22) PCT Filed: Jun. 6, 2006

(86) PCT No.: PCT/SG2006/000144
§ 371 (c)(1),
(2), (4) Date: Dec. 2, 2008

(87) PCT Pub. No.: WO2006/132605
PCT Pub. Date: Dec. 14, 2006

(65) Prior Publication Data
US 2009/0221018 A1 Sep. 3, 2009

(30) Foreign Application Priority Data
Jun. 7, 2005 (SG) ............... SG05/000182

(51) Int. Cl.
C12Q 1/02 (2006.01)
C07K 14/005 (2006.01)
A61K 39/12 (2006.01)
C12N 7/00 (2006.01)
A61K 39/00 (2006.01)

(52) U.S. Cl.
CPC ............. *C07K 14/005* (2013.01); *A61K 39/12* (2013.01); *C12N 7/00* (2013.01); *A61K 2039/5254* (2013.01); *A61K 2039/543* (2013.01); *A61K 2039/552* (2013.01); *C12N 2750/10022* (2013.01); *C12N 2750/10034* (2013.01); *C12N 2750/10061* (2013.01)

(58) Field of Classification Search
None
See application file for complete search history.

(56) References Cited

U.S. PATENT DOCUMENTS

| | | | |
|---|---|---|---|
| 3,770,380 A | 11/1973 | Smith | 436/520 |
| 3,876,504 A | 4/1975 | Koffler | 435/7.92 |
| 4,011,308 A | 3/1977 | Giaevera | 435/5 |
| 4,016,043 A | 4/1977 | Schuurs et al. | 435/5 |
| 4,372,745 A | 2/1983 | Mandle et al. | 436/537 |
| 4,722,890 A | 2/1988 | Sanders et al. | 435/7.4 |
| 4,816,567 A | 3/1989 | Cabilly et al. | 530/387.3 |
| 5,503,974 A | 4/1996 | Gruber et al. | 435/5 |
| 5,747,243 A | 5/1998 | Gruber et al. | 435/5 |
| 6,217,883 B1 * | 4/2001 | Allan et al. | 424/202.1 |
| 6,410,031 B1 | 6/2002 | Kwang et al. | 424/218.1 |
| 6,558,675 B1 | 5/2003 | Oon et al. | 424/227.1 |
| 6,593,082 B1 | 7/2003 | Oon et al. | 435/5 |
| 6,703,023 B1 | 3/2004 | Jestin et al. | 424/204.1 |
| 6,787,142 B2 | 9/2004 | Oon et al. | 424/189.1 |
| 7,037,682 B2 | 5/2006 | Oon et al. | 435/69.1 |
| 7,038,035 B1 | 5/2006 | Oon et al. | 536/23.72 |
| 7,105,165 B2 | 9/2006 | Oon et al. | 424/189.1 |
| 2003/0096377 A1 | 5/2003 | Meng et al. | 435/91.2 |
| 2004/0123349 A1 | 6/2004 | Xie et al. | 800/287 |
| 2004/0209292 A1 | 10/2004 | Oon et al. | 435/6 |
| 2005/0108793 A1 | 5/2005 | Hu et al. | 800/287 |
| 2005/0155116 A1 | 7/2005 | Xie et al. | 800/295 |
| 2006/0143734 A1 | 6/2006 | Yin et al. | 800/279 |
| 2007/0026422 A1 | 2/2007 | Oon et al. | 435/6 |
| 2009/0221018 A1 * | 9/2009 | Kwang et al. | 435/29 |
| 2011/0008871 A1 | 1/2011 | Lau et al. | 435/235.1 |

FOREIGN PATENT DOCUMENTS

| | | |
|---|---|---|
| GB | 2276169 | 9/1994 |
| JP | 2004-503234 | 2/2004 |
| WO | WO 84/03564 | 9/1984 |
| WO | WO 91/00047 | 1/1991 |
| WO | WO 99/29717 | 6/1999 |
| WO | WO 99/66047 | 12/1999 |
| WO | WO 99/66048 | 12/1999 |
| WO | WO 00/18958 | 4/2000 |
| WO | WO 00/18968 | 4/2000 |
| WO | WO 00/77216 | 12/2000 |
| WO | WO 00/78995 | 12/2000 |
| WO | WO 01/96377 | 12/2001 |
| WO | WO 2006/132598 | 12/2006 |
| WO | WO 2006/132605 | 12/2006 |
| WO | WO 2007/123496 | 11/2007 |
| WO | WO 2008/140414 | 11/2008 |

OTHER PUBLICATIONS

Juhan et al, Virus Research, 2010, 147, pp. 60-66.*
Karuppannan et al, Virology, 2009, pp. 338-347.*
Ellis et al. (Canadian Veterinary Journal. 2001; 42: 461-464).*
Chen et al. (Revue Med. Vet. 2007; 158 (8-9): 458-462).*
Hawkes, Aaron. "Detection of Antibodies Against the Open Reading Frame Three Protein of Porcine Circovirus 2 in Pigs." (Jun. 2014).*
Lv et al. (Virus Genes. Aug. 2014; 49 (1): 1-10).*
Genbank Accession No. AY678532 "Porcine circovirus 2 strain ZS0401, complete genome" www.ncbi.nlm.nih.gov/nuccore/50657589 (accessed Apr. 2, 2010), 3 pages.
International Search Report, issued Dec. 13, 2006, in connection with International Patent Application No. PCT/SG2006/000144.
Written Opinion of the International Searching Authority, issued Dec. 13, 2006, in connection with International Patent Application No. PCT/SG2006/000144.
International Preliminary Report on Patentability, issued Aug. 13, 2007, in connection with International Patent Application No. PCT/SG2006/000144.

(Continued)

*Primary Examiner* — Shanon A Foley
(74) *Attorney, Agent, or Firm* — Dentons US LLP; Stephanie Seidman

(57) ABSTRACT

The present invention is based on the ORF3 gene of Porcine Circovirus Type 2 (PCV2) and the identification of tis apoptotic role. This discovery has led to the development of an attenuated live vaccine against PCV2.

9 Claims, 16 Drawing Sheets

(56) References Cited

OTHER PUBLICATIONS

Examination Report, issued May 8, 2008, in connection with corresponding European Patent Application No. 06748096.2.
Examination Report, issued Mar. 30, 2010, in connection with corresponding European Patent Application No. 06748096.2.
Allan, G. and J. Ellis, "Porcine circoviruses: a review," J. Vet. Diagn. Investig. 12:3-14 (2000).
Allan et al., "Pathogenesis of porcine circovirus: experimental infections of colostrum deprived piglets and examination of pig foetal material," Vet. Microbiol. 44:49-64 (1995).
Allan et al., "Experimental reproduction of sever wasting disease by co-infection of pigs with porcine circovirus and porcine parvovirus," J. Comp. Pathol. 121:1-11 (1999).
Altschul, S., "A protein alignment scoring system sensitive at all evolutionary distances," J Mol Evol 36:290-300 (1993).
Altschul et al., "Basic local alignment search tool," J Mol Biol 215:403 (1990).
Ashkenazi, A. and V. Dixit, "Death receptors: signalling and modulation," Science 281: 1305-1308 (1998).
Blanchard et al., "Protection of swine against post-weaning multisystemic wasting syndrome (PMWS) by porcine circovirus type 2 (PCV2) proteins," Vaccine 21:4565-4575 (2003).
Bolin et al., "Postweaning multisystemic wasting syndrome induced after experimental inoculation of cesarean-derived, colostrum-deprived piglets with type 2 porcine circovirus," J. Vet. Diagn. Invest. 13:185-194 (2001).
Budihardjo et al., "Biochemical pathways of caspase activation during apoptosis," Annu. Rev. Cell. Dev. Biol. 15:269-290 (1999).
Chae, C., "Postweaning multisystemic wasting syndrome: a review of aetiology, diagnosis and pathology," Vet. J. 168:41-49 (2004).
Cheung, A., "Comparative analysis of the transcriptional patterns of pathogenic and nonpathogenic porcine circoviruses," Virology 310:41-49 (2003).
Cheung, A., "Transcriptional analysis of porcine circovirus type 2," Virology 305:168-180 (2003).
Cohen, G., "Caspases: the executioners of apoptosis," Biochem. J. 326:1-16 (1997).
Coligan et al., "Immunofluorescence and cell sorting," Current Protocols in Immunology 1(2):Chapter 5 (1991).
Devereux et al., "A comprehensive set of sequence analysis programs for the VAX," Nucleic Acids Research 12:387-395 (1984).
Drew, T., "A review of evidence for immunosuppression due to porcine reproductive and respiratory syndrome virus," Vet. Res. 31:27-39 (2000).
Earshaw et al., "Mammalian caspases: structure, activation, substrates, and functions during apoptosis," Ann. Rev. Biochem. 68:383-424 (1999).
Fenaux et al., "Two amino acid mutations in the capsid protein of type 2 porcine circovirus (PCV2) enhanced PCV2 replication in vitro and attenuated the virus in vivo," J. Virology 78:13440-13446 (2004).
Fenaux et al., "Cloned genomic DNA of type 2 porcine circovirus in infectious when injected directly into the liver and lymph nodes of pigs: characterization of clinical disease, virus distribution, and pathologic lesions," J. Virol. 76:541-551 (2002).
Fenaux et al., "Immunogenicity and pathogenicity of chimeric infectious DNA clones of pathogenic porcine circovirus type (PCV2) and nonpathogenic PCV1 in weaning pigs," J. Virol. 77:11232-11243 (2003).
GenBank Accession Number: AF201897. (5 pages) (accessed Aug. 4, 2008).
GenBank Accession Number: AY291317. (3 pages) (accessed Aug. 4, 2008).
Genbank Accession Number: AY847748. (2 pages) (accessed Aug. 4, 2008).
Green, D., "Apoptotic pathways: the roads to ruin," Cell 94:695-698 (1998).
Janicke et al., "Caspase-3 is required for DNA fragmentation and morphological changes associated with apoptosis," J. Biol. Chem. 273:9357-9360 (1998).

Jeurissen et al., "Chicken anemia virus causes apoptosis of thymocytes after in vivo infection and of cell lines after in vitro infection," J. Virol. 66:7383-7388 (1992).
Kamstrup et al., "Immunisation against PCV2 structural protein by DNA vaccine of mice," Vaccine 22:1358-1361 (2004).
Karlin, S. and S. Altschul, "Applications and statistics for multiple high-scoring segments in molecular sequences," Proc. Nad. Acad. Sci. USA 90:5873-5877 (1993).
Kennedy et al., "Reproduction of lesions of postweaning multisystemic wasting syndrome by infection of conventional pigs with porcine circovirus type 2 alone or in combination with porcine pawovirus," J. Comp. Pathol. 122:9-24 (2000).
Kiupel et al., "Viral replication and lesions in BALBlc mice experimentally inoculated with porcine circovirus isolated from a pig with postweaning multisystemic wasting disease," Vet. Pathol. 38:74-82 (2001).
Kohler, G. and C. Milstein, "Continuous cultures of fused cells secreting antibody of predefined specificity," Nature 256:495-497 (1975).
Lekcharoensuk et al., "Epitope mapping of the major capsid protein of type 2 porcine circovirus (PCV2) by using chimeric PCV1 and PCV2," J. Virol. 78:8135-8145 (2004).
Liu et al., "The ORF3 protein of porcine circovirus type 2 is involved in viral pathogenesis in vivo," J. Virol 80:5065-5073 (2006).
Liu et al., "Characterization of a previously unidentified viral protein in porcine circovirus type 2-infected cells and its role in virus-induced apoptosis," J. Virol. 79:8262-8274 (2005).
Liu et al., "The ORF3 protein of porcine circovirus type 2 interacts with porcine ubiquitin E3 ligase Pirh2 and facilitates p53 expression in viral infection," J. Virol. 81:9560-9567 (2007).
Liu et al., "Avian encephalomyelitis virus induces apoptosis via major structural protein VP3," Virology 300:39-49 (2002).
Liu et al., "Avian encephalomyelitis virus nonstructural protein 2C induces apoptosis by activating cytochrome c/caspase-9 pathway," Virology 318:169-182 (2004).
Liu et al., "Membrane-association properties of avian encephalomyelitis virus protein 3A," Virology 321:297-306 (2004).
Liu et al., "Inhibition of porcine circovirus type 2 replication in mice by RNA interference," Virology 347:422-433 (2006).
Liu et al., "Antigenic and molecular characterization of recent infectious bursal disease virus isolates in China," Virus Genes 24:135-147 (2002).
Liu et al., "Nuclear localization of the ORF2 protein encoded by porcine circovirus type 2," Virology 285:91-99 (2001).
Mandrioli et al., "Apoptosis and proliferative activity in lymph node reaction in postweaning multisystemic wasting syndrome (PMWS)," Vet. Immunol. Immunopathol. 97:25-37 (2004).
Mankertz et al., "Identification of a protein essential for replication of porcine circovirus," J. Gen. Virol. 79:381-383 (1998).
Mankertz et al., "Molecular biology of porcine circovirus: analyses of gene expression and viral replication," Vet. Microbiol. 98:81-88 (2004).
Meehan et al., "Sequence of porcine circovirus DNA: Affinities with plant cicoviruses," J. Gen. Virol. 78:221-227 (1997).
Miyata et al., "Identification of a novel GC-rich 113-nucleotide region to complete the circular, single-stranded DNA genome of TT virus, the first human circovirus," J. Virol. 73:3582-3586 (1999).
Mundt et al., "Vp5 of infectious bursal disease virus is not essential for viral replication in cell culture," J. Virol. 71:5647-5651 (1997).
Nawagitgul et al., "Open reading frame 2 of porcine circovirus type 2 encodes a major capsid protein," J. Gen. Virol. 81:2281-2287 (2000).
Nawagitgul et al., "Modified indirect porcine circovirus (PCV) type 2-based and recombinant capsid protein (ORF2)-based enzyme-linked immunosorbent assay for detection of antibodies to PCV," Clin. Diagn. Lab. Immunol. 9:33-40 (2002).
Needleman, S. and C. Wunsch, "A general method applicable to the search for similarities in the amino acid sequence of two proteins," Journal of Molecular Biology 48:443-453 (1970).
Nicholson et al., "Identification and inhibition of the ICE/CED-3 protease necessary for mammalian apoptosis," Nature 376:37-43 (1995).

(56) References Cited

OTHER PUBLICATIONS

Nishizawa et al., "A novel DNA virus (TTV) associated with elevated transaminase levels in posttransfusion hepatitis of unknown etiology," Biochem. Biophys. Res. Commun. 241:92-97 (1997).
Noteborn et al., "A single chicken anemia virus protein induces apoptosis," J. Virol. 68:346-351 (1994).
Phenix et al., "Nucleotide sequence analysis of a novel circovirus of canaries and its relationship to other members of the genus Circovirus of the family Circoviridae," J. Gen. Virol. 82:2805-2809 (2001).
Pringle, C. "Virus taxonomy at the XIth International Congress of Virology, Sydney, Australia," Arch. Virol. 144:2065-2070 (1999).
Resendes et al., "Apoptosis in lymphoid organs of pigs naturally infected by porcine circovirus type 2," J. Gen. Virol. 85:2837-2844 (2004).
Riechmann et al., "Reshaping human antibodies for therapy," Nature 332:323-327 (1988).
Ritchie et al., "Characterization of a new virus from cockatoos with psittacine beak and feather disease," Virology 171:83-88 (1989).
Roulston et al., "Virus and apoptosis," Annu. Rev. Microbiol. 53:577-628 (1999).
Salvesen et al., "Caspases: intracellular signaling by proteolysis," Cell 91:443-446 (1997).
Scatchard, G., "The attractions of proteins for small molecules and ions," Ann. NY Acad. Sci. 51:660-672 (1949).
Schulze-Osthoff et al., "Apoptosis signalling by death receptors," Eur. J. Biochem. 254:439-459 (1998).
Segales et al., "Immunosuppression in postweaning multisystemic wasting syndrome affected pigs," Vet. Microb. 98:151-158 (2004).
Shibahara et al., "Porcine circovirus induces B lymphocyte depletion in pigs with wasting disease syndrome," J. Vet. Med. Sci. 62:1125-1131 (2000).
Takahashi et al., "Identification of a new human DNA virus (TTV-like mini virus, TLMV) intermediately related to TT virus and chicken anemia virus," Arch. Virol. 145:979-993 (2000).
Telford et al., "Comparative evaluation of several DNA binding dyes in the detection of apoptosis-associated chromatin degradation by flow cytometry," Cytometry 13:137-143 (1992).
Teodoro, J. and P. Branton "Regulation of apoptosis by viral gene products," J. Virol. 71: 1739-1746 (1997).
Tischer et al., "Replication of porcine circovirus: induction by glucosamine and cell cycle dependence," Arch. Virol. 96:39-57 (1987).
Tischer et al., "A very small porcine virus with circular single-stranded DNA," Nature 295:64-66 (1982).
Tischer et al., "Studies on epidemiology and pathogenicity of porcine circovirus," Arch. Virol. 91:271-276 (1986).
Todd et al., "Comparison of three animal viruses with circular single-stranded DNA genomes," Arch. Virol. 117:129-135 (1991).
Todd et al., "Genome sequence determinations and analyses of novel circoviruses from goose and pigeon," Virology 286:354-362 (2001).
Verhoeyan et al., "Reshaping human antibodies:Grafting an antilysozyme activity," Science 239:1534-1536 (1988).
Wei et al., "Porcine circovirus type 2 induces the activation of nuclear factor kappa B by IkappaBalpha degradation," Virology 378:177-184 (2008).
Winter, G. and C. Milstein, "Man-made antibodies," Nature 349: 293-299 (1991).
Woods et al., "Circovirus-like infection in a pigeon," J. Vet. Diagn. Invest. 5:609-612 (1993).
Yao, K., and V. Vakharia,"Induction of apoptosis in vitro by the 17-kDa nonstructural protein of infectious bursal disease virus: possible role in viral pathogenesis," Virology 285:50-58 (2001).
Zhu et al., "Enhanced replication of porcine circovirus type 2 (PCV2) in a homogeneous subpopulation of PK15 cell line," Virology 369:423-430 (2007).
de Boisseson et al., "Molecular characterization of Porcine circovirus type 2 isolates from post-weaning multisystemic wasting syndrome-affected and non-affected pigs," J Gen Virol 85:293-304 (2004).
de Saint Jean et al., "Fas- and Interferon Gamma-Induced Apoptosis in Chang Conjunctival Cells: Further Investigations," Invest Ophthalmol Vis Sci 41:2531-2543 (2000).
Ellis et al., "Isolation of circovirus from lesions of pigs with postweaning multisystemic wasting syndrome" Can Vet J 39:44-51 (1998).
Jakel, C. "The Unique Chimeric Formulation of Suvaxyn® PCV 2 One Dose," Technical Review, 2 pages (Jun. 2007).
Karuppannan, A. and J. Kwang, "ORF3 of porcine circovirus 2 enhances the in vitro and in vivo spread of the virus," Virology 410: 248-256 (2011).
Karuppanan et al., "Porcine circovirus type 2 ORF3 protein competes with P53 in binding to Pirh2 and mediates the deregulation of P53 homeostasis," Virology 398:1-11 (2010).
Kiupel et al. 2"Porcine Circovirus type 2 (PCV2) causes apoptosis in inoculated BALB/c mice," BMC Veterinary Research 1:7, 8 pages (2005).
Li et al., "A mouse model to study infection against porcine circovirus type 2: viral distribution and lesions in mouse," Virology Journal 7:158, 6 pages (2010).
Timmusk et al., "Phylogenetic analysis of porcine circovirus type 2 (PCV2) pre- and post-epizootic postweaning multisystemic wasting syndrome (PMWS)," Virus Genes 36(3):509-520 (2008).
Wu et al., "RRR-α-tocopheryl succinate inhibits human gastric cancer SGC-7901 cell growth by inducing apoptosis and DNA synthesis arrest?," World J Gastroenterol 8(1):26-30 (2002).
Office Action with English translation, issued Dec. 27, 2012, in connection with corresponding Thai Patent Application No. 0601002591, 7 pages.
Letter/Written Disclosure of the Supplemental Information Disclosure Statement for the above-referenced application, mailed on Apr. 5, 2012, 2 pages.
Office Action, issued Mar. 9, 2011 for Chinese Patent Application No. 200680020344.2 [English translation], 7 pages.
Office Action, received Dec. 30, 2011, in connection with Taiwanese Patent Application No. 95120044 [English translation], 6 pages.
Office Action, issued Feb. 3, 2012, in connection with Korean Patent Application No. 10-2007-7030944 [English translation], 5 pages.
English Translation of Office Action, issued for corresponding Japanese Patent Application No. 2008-515665, received Oct. 21, 2011, 6 pages.
Office Action, issued Oct. 26, 2009, in connection with corresponding Australian Patent Application No. 2006255818. 2 pages.
Office Action, issued Jun. 11, 2010, in connection with corresponding Australian Patent Application No. 2006255818. 2 pages.
Office Action, issued Jun. 11, 2010, in connection with corresponding Vietnamese Patent Application No. 1-2008-00040. 4 pages.
Letter/Written Disclosure of the Supplemental Information Disclosure Statement for the above-referenced application, mailed Oct. 30, 2014, 2 pages.
Notice of Acceptance, issued Nov. 11, 2010, in connection with corresponding Australian Patent Application No. 2006255818, 3 pages.
Office Action, issued Mar. 29, 2012, in connection with corresponding Chinese Patent Application No. 200680020344.2 [English translation and original document in Chinese], 10 pages.
Response, dated Oct. 7, 2010, to Examination Report, issued Mar. 30, 2010, in connection with corresponding European Patent Application No. 06748096.2, 10 pages.
Examination Report, issued Mar. 21, 2012, in connection with corresponding European Patent Application No. 06748096.2, 10 pages.
Response, dated Jul. 31, 2012, to Examination Report, issued Mar. 21, 2012, in connection with corresponding European Patent Application No. 06748096.2, 10 pages.
Examination Report, issued Sep. 24, 2012, in connection with corresponding European Patent Application No. 06748096.2, 16 pages.
Response, dated Dec. 20, 2012, to Examination Report, issued Sep. 24, 2012, in connection with corresponding European Patent Application No. 06748096.2, 11 pages.

(56) References Cited

OTHER PUBLICATIONS

Communication under Rule 71(3) Intention to Grant, issued Mar. 18, 2013, in connection with corresponding European Patent Application No. 06748096.2, 5 pages.

Office Action, issued Sep. 24, 2012, in connection with corresponding Korean Patent Application No. 10-2007-7030944 [English translation and original document in Chinese], 6 pages.

Office Action, issued Oct. 30, 2008, in connection with corresponding Thai Patent Application No. 0601002591 [English translation and original document in Thai], 2 pages.

Second Office Action, issued Jun. 4, 2012, in connection with corresponding Taiwanese Patent Application No. 95120044 [English translation and original document in Chinese], 8 pages.

Letter/Written Disclosure of the Supplemental Information Disclosure Statement for the above-referenced application, filed herewith on Dec. 7, 2015, 2 pages.

Hawkes, A., "Detection of antibodies against the open reading frame three protein of porcine circovirus 2 in Pigs," (A Thesis for the Degree of Master of Science, Veterinary Medical Sciences, Calgary, Alberta, Jun. 2014) 114 pages.

Lv et al., "Current understanding of genomic DNA of porcine circovirus type 2," Virus Genes 49(1): 1-10 (2014).

* cited by examiner

Fig. 1B

Construction of PCV2 mutant lacking ORF3 gene

→ ORF1
644                    671        680
-TAGAAACAAGTGGTGGGATGGTTACCATGGTGAAGAA-
-ATCTTTGTTCACCACCCTACCAATGGTACCACTTCTT-
                                    ← ORF3

→

→ ORF1
644                    671        680
-TAGAAACAAGTGGTGGGATGGTTACCACGGTGAAGAA-
-ATCTTTGTTCACCACCCTACCAATGGTGCCACTTCTT-
                                 ←//← ORF3

ORF1: CAT → CAC, Histidine → Histidine
ORF3: deleted

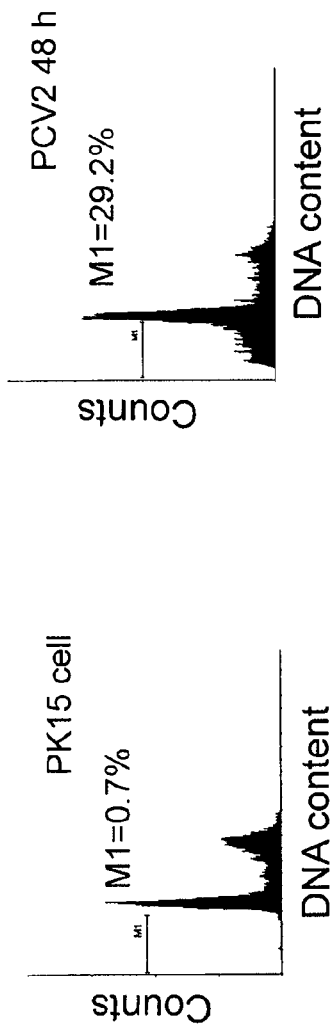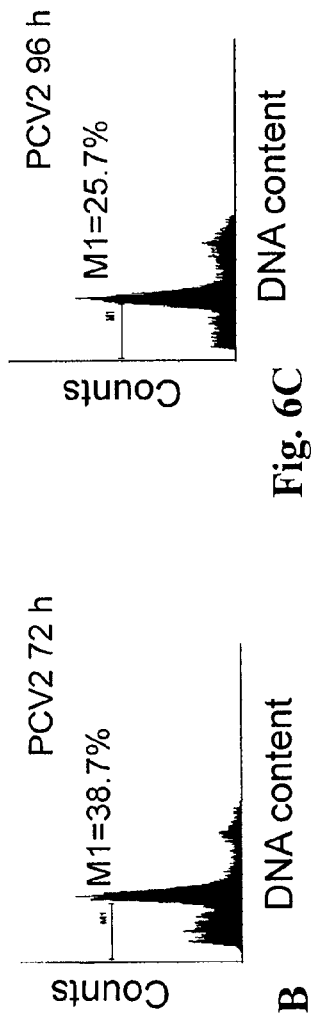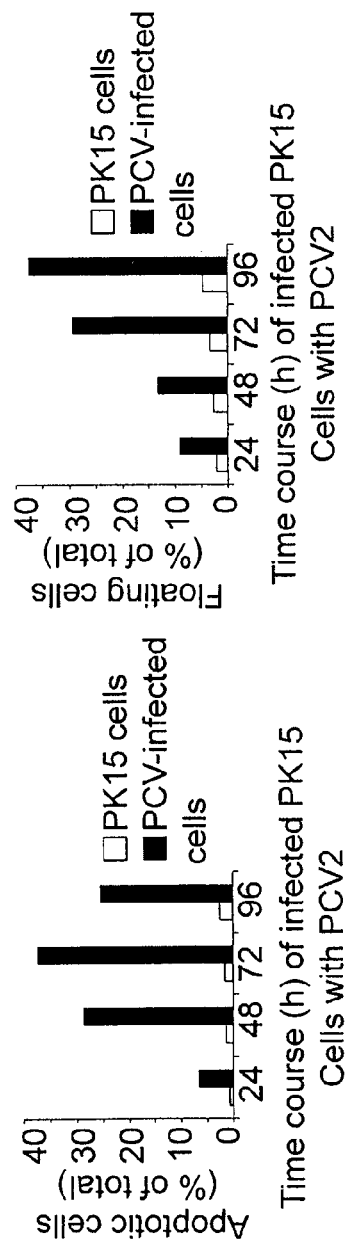
Fig. 6A
Fig. 6B
Fig. 6C

ACCAGCGCACTTCGGCAGCGGCAGCACCTCGGCAGCACCTCAGCAGCAAC
ATGCCCAGCAAGAAGAATGGAAGAAGCGGACCCCAACCACACAAAAGGT
GGGTGTTCACGCTGAATAATCCTTCCGAAGACGAGCGCAAGAAAATACGG
GAGCTTCCAATCTCCCTTTTTGATTATTTTATTGTTGGCGAGGAGGGTAAT
GAGGAAGGACGAACACCCCACCTCCAGGGGTTCGCTAATTTTGTGAAGAA
GCAAACATTTAATAAAGTGAAATGGTATTTCGGTGCCCGCTGCCACATCG
AGAAAGCGAAAGGAACTGATCAGCAGAATAAAGAATACTGCAGTAAAGA
AGGCAACTTACTGATAGAATGTGGAGCTCCTAGATCTCAAGGACAACGGA
GTGACCTGTCTACTGCTGTGAGTACCTTGTTGGAGAGCGGGAGTCTGGTG
ACCGTTGCAGAGCAGCACCCTGTAACGTTTGTCAGAAATTTCCGCGGGCT
GGCTGAACTTTTGAAAGTGAGCGGGAAAATGCAGAAGCGTGATTGGAAG
ACGAATGTACACGTCATTGTGGGCCACCTGGTTGTGGTAAAAGCAAATG
GGCTGCTAATTTTGCAGACCCGGAAACCACATACTGGAAACCACCTAGAA
ACAAGTGGTGGGATGGTTACCATGGTGAAGAAGTGGTTGTTATTGATGAC
TTTTATGGCTGGCTGCCCTGGGATGATCTACTGAGACTGTGTGATCGATAT
CCATTGACTGTAGAGACTAAAGGTGGAACTGTACCTTTTTGGCCCGCAGT
ATTCTGATTACCAGCAATCAGACCCCGTTGGAATGGTACTCCTCAACTGCT
GTCCCAGCTGTAGAAGCTCTTTATCGGAGGATTACTTCCTTGGTATTTTGG
AAGAATGCTACAGAACAATCCACGGAGGAAGGGGGCCAGTTCGTCACCCT
TTCCCCCCCATGCCCTGAATTTCCATATGAAATAAATTACTGAGTCTTTTTT
ATCACTTCGTAATGGTTTTTATTATTTATTAAGGGTTAAGTGGGGGGTCTT
TAAGATTAAATTCTCTGAATTGTACATACATGGTTACACGGATATTGTATT
CCTGGTCGTATATACTGTTTTCGAACGCAGTGCCGAGGCCTACGTGGTCTA
CATTTCCAGCAGTTTGTAGTCTCAGCCACAGCTGATTTCTTTTGTTGTTTGG
TTGGAAGTAATCAATAGTGGAATCTAGGACAGGTTTGGGGGTAAAGTAGC
GGGAGTGGTAGGAGAAGGGCTGGGTTATGGTATGGCGGGAGGAGTAGTT
TACATAGGGGTCATAGGTGAGGGCTGTGGCCTTTGTTACAAAGTTATCATC
TAGAATAACAGCACTGGAGCCCACTCCCCTGTCACCCTGGGTGATCGGGG
AGCAGGGCCAGAATTCAACCTTAACCTTTCTTATTCTGTAGTATTCAAAGG
GCACAGAAGCGGGGGTTTGAGCCCCTCCTGGGGAAGAAAATCATTAAT
ATTGAATCTATCATGTCCACCGCCCAAGAGGGCGTTTTGACTGTGGTTCGC
TTGATAGTATATCCGAAGGTGCGGGAGAGGCGGGTGTTGAAGATGCCATT
TTTCCTTCTCCAGCGGTAACGGTGGCGGGGGTGGACGAGCCAGGGGCGGC
GGCGGAGGATCTGGCCAAGATGGCTGCGGGGGCGGTGTCTTCTTCTCCGG
TAACGCCTCCTTGGATACGTCATATCTGAAAACGAAAGAAGTGCGCTGTA
AGTATT

Figure 12
ATGGTAACCATCCCACCACTTGTTTCTAGGTGGTTTCCAGTATGTGGTTTC
CGGGTCTGCAAAATTAGCAGCCCATTTtgaTTTACCACAACCAGGTGGCCCC
ACAATGACGTGTACATTCGTCTTCCAATCACGCTTCTGCATTTTCCCGCTC
ACTTTCAAAAGTTCAGCCAGCCCGCGGAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

Figure 13
ATGGTAACCATCCCACCACTTGTTTCTAGGTGGTTTCCAGTATGTGGTTTC
CGGGTCTGCAAAATTAGCAGCCCATTTGCTTTTACCACAACCAGGTGGCCC
CACAATGACGTGTACATTCGTCTTCCAATCACGCTTCTGCATTTTCCCGCTg
ACTTTCAAAAGTTCAGCCAGCCCGCGGAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

Figure 14
AATGGTAACCATCCCACCACTTGTTTCTAGGTGGTTTCCAGTATGTGGTTTC
CGGGTCTGCAAAATTAGCAGCCCATTTGCTTTTACCACAACCAGGTGGCCC
CACAATGACGTGTACATTCGTCTTCCAATCACGCTTCTGCATTTTCCCGCT
CACTTTCAAAAGTTCAGCCAGCCCGCGaAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

Figure 15
ATGGTAACCATCCCACCACTTGTTTCTAGGTGGTTTCCAGTATGTGGTTTC
CGGGTCTGCAAAATTAGCAGCCCATTTGCTTTTACCACAACCAGGTGGCCC
CACAATGACGTGTACATTCGTCTTCCAATCACGCTTCTGCATTTTCCCGCT
CACTTTCAAAAGTTCAGCCAGCCCGCGGAAATTTCTGACAAACGTTACAG
GGTGCTGCTCTGCAACGGTCACCAGACTCCCGCTCTCCAACAAGGTACTtA
CAGCAGTAGACAGGTCACTCCGTTGTCCTTGAGATCTAGGAGCTCCACATT
CTATCAGTAA

Figure 16 gTGGTAACCATCCCACCACTTGTTTCTAGGTGGTTTCCAGTATGTGGTTTCC
GGGTCTGCAAAATTAGCAGCCCATTTtgaTTTACCACAACCAGGTGGCCCC
ACAATGACGTGTACATTCGTCTTCCAATCACGCTTCTGCATTTTCCCGCTC
ACTTTCAAAAGTTCAGCCAGCCCGCGGAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

Figure 17 gTGGTAACCATCCCACCACTTGTTTCTAGGTGGTTTCCAGTATGTGGTTTCC
GGGTCTGCAAAATTAGCAGCCCATTTGCTTTTACCACAACCAGGTGGCCCC
ACAATGACGTGTACATTCGTCTTCCAATCACGCTTCTGCATTTTCCCGCTC
ACTTTCAAAAGTTCAGCCAGCCCGCGaAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

Figure 18 gTGGTAACCATCCCACCACTTGTTTCTAGGTGGTTTCCAGTATGTGGTTTCC
GGGTCTGCAAAATTAGCAGCCCATTTtgaTTTACCACAACCAGGTGGCCCC
ACAATGACGTGTACATTCGTCTTCCAATCACGCTTCTGCATTTTCCCGCTC
ACTTTCAAAAGTTCAGCCAGCCCGCGaAAATTTCTGACAAACGTTACAGG
GTGCTGCTCTGCAACGGTCACCAGACTCCCGCTCTCCAACAAGGTACTCAC
AGCAGTAGACAGGTCACTCCGTTGTCCTTGAGATCTAGGAGCTCCACATTC
TATCAGTAA

PORCINE CIRCOVIRUS TYPE 2 VACCINES

This application is the National Stage of International Application No. PCT/SG2006/000144, filed 6 Jun. 2006, and claims benefit of priority under 35 U.S.C. §365(b) to Application No. PCT/SG2005/000182, filed 7 Jun. 2005. The subject matter of each of the above-noted applications is incorporated herein by reference in its entirety.

A Sequence Listing, incorporated by reference in its entirety, is provided on identical compact discs (labeled COPY 1 REPLACEMENT 04/03/2009, COPY 2 REPLACEMENT 04/03/2009, and Computer-readable form (CRF) REPLACEMENT 04/03/2009), each compact disc containing the file 2511USSEQ.002.txt, created on Apr. 3, 2009, and 11 kilobytes in size.

FIELD OF THE INVENTION

The present invention relates to the creation of novel Porcine Circovirus Type 2 (PCV2) viruses and the provision of vaccines against the same.

All documents cited in this text ("herein cited documents") and all documents cited or referenced in the herein cited documents are hereby incorporated herein by reference for all purposes.

There is no admission that any of the various documents cited in this text are prior art as to the present invention.

BACKGROUND OF THE INVENTION

Postweaning Multisystemic Wasting Syndrome (PMWS)

PMWS is an emerging disease affecting nurseries and post-weaning pigs, now endemic in many swine-producing countries, causing a potential economical impact on the swine industry worldwide. PMWS primarily affects pigs between 5 and 18 weeks of age, although the disease has been described in 4-20 week-old pigs (42). Clinical PMWS signs include progressive weight loss, dyspnoea, tachypnea, anaemia, diarrhoea, and jaundice. Mortality rate may vary from 1 to 2% up to 30% in complicated cases.

Porcine circovirus (PCV) was originally identified as a contaminant of porcine kidney cell cultures (PK15 ATCC CCL-33) (47). The PCV virion is icosahedral, non-enveloped, and 17 nm in diameter with a single-stranded circular DNA of about 1.76 kb. PCV is classified in the genus *Circovirus* of the Circoviridae family, which consists of other animal circoviruses such as psittacine beak-feather disease virus, goose circovirus, canary circovirus, and pigeon circovirus (35, 38, 50, 51, 52). Two genotypes of PCV have been recognized. The PK15 cell-derived PCV has been considered to be nonpathogenic to pigs (3, 48), and is designated PCV type 1 (PCV1). Serologic surveys indicated that PCV1 is widespread in swine, but no known animal disease has been associated with PCV1. On the other hand, PCV type 2 (PCV2) is now accepted as the major infectious agent involved in postweaning multisystemic wasting syndrome (PMWS) (2, 6, 20), a new emerging swine disease worldwide since its occurrence in Canada in 1991 (1, 8).

PCV2 and its Mode of Action

Apoptosis is an active physiological process of cellular self-destruction with specific morphological and biochemical changes (39). Many viruses induce apoptosis as part of their natural life cycle (39). On the one hand, apoptosis may be an important mechanism for the release and dissemination of host cell-produced progeny virions by minimizing inflammatory or immune responses to the viral agent. On the other hand, virus-induced apoptosis could be regarded as a defense strategy of multicellular host organisms for the purposeful destruction of infected cells. Most viruses that lead to apoptotic cell death trigger the activation of the caspase cascade for the execution process of the death program. Apoptosis has been proposed as the mechanism that is responsible for B-cell depletion in naturally PMWS-affected pigs (43), but contradictory results have recently been reported that lymphocyte apoptosis is not a prevalent phenomenon in the development of PMWS lymphoid-depletion lesions (24, 37).

The overall DNA sequence homology within the PCV1 or PCV2 isolates is greater than 90%, while the homology between PCV1 and PCV2 isolates is 68-76%. Two major open reading frames (ORFs) have been recognized for PCV-ORF1, also known as the rep gene, encodes a protein of 35.7 kDa involved in virus replication (26), and ORF2, the cap gene, encodes the major immunogenic capsid protein of 27.8 kDa (9, 30, 31). In addition to the replicase ORF1 and the capsid protein ORF2, it is predicted to contain another five potential ORFs encoding proteins larger than 5 kDa by computer searching (27). Whether these potential ORFs are expressed or not and whether the expressed proteins are essential for viral replication awaits elucidation.

For PCV2, the largest among the five ORFs above is a fragment of 315 bp in length, named ORF3 here, which does not show similarities to any known protein. In contrast, the ORF fragment located in the corresponding region of PCV1 is 612 bp in length, much longer than ORF3 in PCV2. Furthermore, there is only 61.5% amino acid identity between the ORF3 of PCV2 and the corresponding region of PCV1. Whether this variation is associated with PCV2 pathogenicity has yet to be determined.

Histopathological findings and features of the disease from PMWS-affected pigs suggest that PCV2, in some conditions, maybe a cause of secondary immunodeficiency in pigs. Microscopic lesions are characterized by lymphocyte depletion of follicular and interfollicular areas together with macrophage infiltration of lymphoid tissues in PMWS-affected pigs. Moreover, co-infections of other infectious agents with PCV2, increase the occurrence and severity of the disease. (2,3)

PMWS is currently still a major problem in the swine industry worldwide as mortality is still considerable in some farms. Although there is some information on the development of DNA vaccines or subunit vaccines against PCV2, the potential and protective efficacy of live, attenuated vaccines towards certain pathogens should still be of important considerations. There is still no known attenuated live vaccine effective in preventing the spread of this disease.

Currently there are two known vaccines available: the ORF2 recombinant subunit vaccine and a DNA vaccine. Although both vaccines are effective in completely inhibiting the replication of PCV2, the lack of advantageous attributes lowers their commercial value as an effective vaccine against PCV2. The DNA vaccine is able to induce both humoral and cellular responses in pigs but lacks a is proper delivery system to allow a proper administration of the vaccine. This could have affected its efficiency in reducing PCV2 infection, which was only visible at 3 weeks postinfection (5). Although the subunit vaccine works more efficiently against PCV2, it could only stimulate a humoral immunity. The low concentration of protein obtained through the use of the baculovirus system also means multiple dosages are required for immunizing the animal against PCV2, thus decreasing its efficiency. Also, significant growth retardation of the experimental animals was still prominent during the third and fourth week after PCV2 infection. Furthermore, the prime-boost protocol for both vaccines has yet to be determined.

Consequently there is a need for an improved vaccine to combat PMWS.

SUMMARY

The present invention is based on the detection of the ORF3 gene and the identification of its apoptotic role in the virus. This discovery has led to the development of an attenuated live vaccine against PCV2.

A first aspect of the invention provides an immunogenic attenuated PCV2 virus wherein the attenuation is attributable at least in part to aberrant ORF3 expression.

A second aspect of the invention provides a vaccine comprising an immunologically effective amount of a virus according to the first aspect of the invention.

A third aspect of the invention provides a method of inducing an immune response against PCV2, the method comprising administering to a subject the vaccine of the second aspect of the invention.

A fourth aspect of the invention provides a virus of the first aspect of the invention for use in medicine.

A fifth aspect of the invention provides a virus for inducing both humoral and cellular immune response in a subject against PCV2.

A sixth aspect of the invention provides the use of a virus according to the first aspect of the invention in the manufacture of a medicament for inducing an immune response in a subject against PCV2.

A seventh aspect of the invention provides a host cell for production of a virus according to the first aspect of the invention.

An eighth aspect of the invention provides a method of treatment using the virus according to the first aspect of the invention, the method comprising administering an immunologically effective amount of a virus to said animal.

A ninth aspect of the invention provides a method for the production of a virus according to the first aspect of the invention, the method comprising growing a host cell of the seventh aspect of the invention under suitable conditions in a manner allowing production of the virus.

A tenth aspect of the invention provides a protein which is capable of inducing apoptosis. In one embodiment, the protein comprises the amino acid sequence as set forth in SEQ ID NO. 1: MVTIPPLVSRWFP VCGFRVCKISSPFAFTTTRW-PHNDVYIRLPITLLHFPAHFQKFSQPAEISDKRYR VLLCNGHQTPALQQGTHSSRQVTPLSLRSRSSTFYQ An eleventh aspect of the invention provides a nucleic acid molecule which encodes a protein of the tenth aspect of the invention.

In one embodiment, the nucleic acid molecule comprises the sequence set forth in SEQ ID NO. 2:

ATGGTAACCATCCCACCACTTGTTTCTAGGTGGTTTCCAGTATGTGGTTT

CCGGGTCTGCAAAATTAGCAGCCCATTTGCTTTTACCACAACCAGGTGGC

CCCACAATGACGTGTACATTCGTCTTCCAATCACGCTTCTGCATTTTCCC

GCTCACTTTCAAAAGTTCAGCCAGCCCGCGGAAATTTCTGACAAACGTTA

CAGGGTGCTGCTCTGCAACGGTCACCAGACTCCCGCTCTCCAACAAGGTA

CTCACAGCAGTAGACAGGTCACTCCGTTGTCCTTGAGATCTAGGAGCTCC

ACATTCTATCAGTAA

A twelfth aspect of the invention provides a nucleic acid molecule comprising a mutated version of the nucleic acid molecule according to the eleventh aspect of the invention, the nucleic acid molecule being mutated such that there is aberrant expression of the protein encoded by the nucleic acid molecule.

A thirteenth aspect of the invention provides a protein encoded by a nucleic acid molecule of the twelfth aspect of the invention.

A fourteenth aspect of the invention provides a vector, virus or host cell which comprises a nucleic acid molecule according to the eleventh or twelfth aspect of the invention.

A fifteenth aspect of the invention provides an antibody capable of binding to a protein of the tenth or thirteenth aspect of the invention.

A sixteenth aspect of the invention provides a method of generating an antibody which is capable of binding to a protein of the tenth or thirteenth aspect of the invention.

A seventeenth aspect of the invention provides a pharmaceutical composition comprising a nucleic acid molecule, protein, antibody, antagonist, agonist, virus, vector or host cell of the invention.

An eighteenth aspect of the invention provides a method for identifying an agonist or antagonist of a protein of the tenth aspect of the invention.

The method may comprise:
(i) contacting a test compound with a protein of the tenth aspect of the invention and determining if the test compound enhances or decreases the ability of the protein to induce apoptosis; or
(ii) expressing in a cell a protein of the tenth aspect of the invention and exposing the cell to a test compound and determining if the test compound enhances or decreases the ability of the protein to induce apoptosis.

A nineteenth aspect of the invention provides an agonist or antagonist identified by the eighteenth aspect of the invention.

A twentieth aspect of the invention provides a method for screening at least one candidate molecule for its capacity to induce postweaning multisystemic wasting syndrome.

The method may comprise:
(i) contacting the at least one candidate molecule with a biological sample; and
(ii) assaying for the level of apoptosis induced in the biological sample by the at least one candidate molecule. The level of apoptosis is indicative of the capacity of the at least one candidate molecule to induce postweaning multisystemic wasting syndrome.

In one embodiment, the method further comprises the step of determining if a candidate molecule enhances or decreases the ability of the protein to induce apoptosis.

GLOSSARY OF TERMS

This section is intended to provide guidance on the interpretation of the words and phrases set forth below (and where appropriate grammatical variants thereof).

As used in this application, the singular form "a," "an," and "the" include plural references unless the context clearly dictates otherwise. For example, the term "an agent" includes a plurality of agents, including mixtures thereof.

As used herein, the term "comprising" means "including." In the context of this specification, the term "comprising" means "including principally, but not necessarily solely". Variations of the word "comprising", such as "comprise" and "comprises," have correspondingly varied meanings.

The term "vaccine" as used herein includes an agent which may be used to stimulate the immune system of an animal. In this way, immune protection may be provided against an antigen not recognized as a self-antigen by the immune system.

The term "immunization" includes the process of delivering an immunogen to a subject. Immunization may, for example, enable a continuing high level of antibody and/or cellular response in which T-lymphocytes can kill or suppress the pathogen in the immunized animal, which is directed against a pathogen or antigen to which the animal has been previously exposed.

The term "protein" means a polymer made up of amino acids linked together by peptide bonds. The terms "protein" and "polypeptide" are used interchangeably herein, although for the purposes of the present invention a "polypeptide" may constitute a portion of a full length protein such as a functional or active fragment thereof. Alternatively the term "protein" may also constitute a functional variant.

The term "polynucleotide" as used herein refers to a single- or double-stranded polymer of deoxyribonucleotide, ribonucleotide bases or known analogues or natural nucleotides, or mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise indicated, all technical and scientific terms used herein have the same meaning as commonly understood to one of ordinary skill in the art to which the invention belongs.

DESCRIPTION OF THE DRAWINGS

FIG. 6 PCV2-induced apoptotic cells were quantitatively determined. (A) Representative figures of the determination of apoptosis by propidium iodide staining and flow cytometry of PK15 cells infected with the PCV2 strain BJW. For each panel, the percentage of PK15 cells with hypodiploid (apoptotic) DNA content is indicated (M1). B shows the average percentage of apoptosis of three experiments shown in A. C shows the average percentage of detached cells of three experiments in the time indicated.

FIG. 9 Sequence information of the PCV2 viral genome.

FIG. 12 DNA sequence of ORF3 Mutant 27. Mutation points shown in low case font.

FIG. 13 DNA sequence of ORF3 Mutant 52. Mutation points shown in low case font.

FIG. 14 DNA sequence of ORF3 Mutant 61. Mutation points shown in low case font.

FIG. 15 DNA sequence of ORF3 Mutant 85. Mutation points shown in low case font.

FIG. 16 DNA sequence of ORF3 Double Mutant ATG & 27. Mutation points shown in low case font.

FIG. 17 DNA sequence of ORF3 Double Mutant ATG & 61. Mutation points shown in low case font.

FIG. 18 DNA sequence of ORF3 Triple Mutant ATG, 27 & 61. Mutation points shown in low case font.

DETAILED DISCLOSURE OF EMBODIMENTS

The Attenuated Virus

Figure 1A:
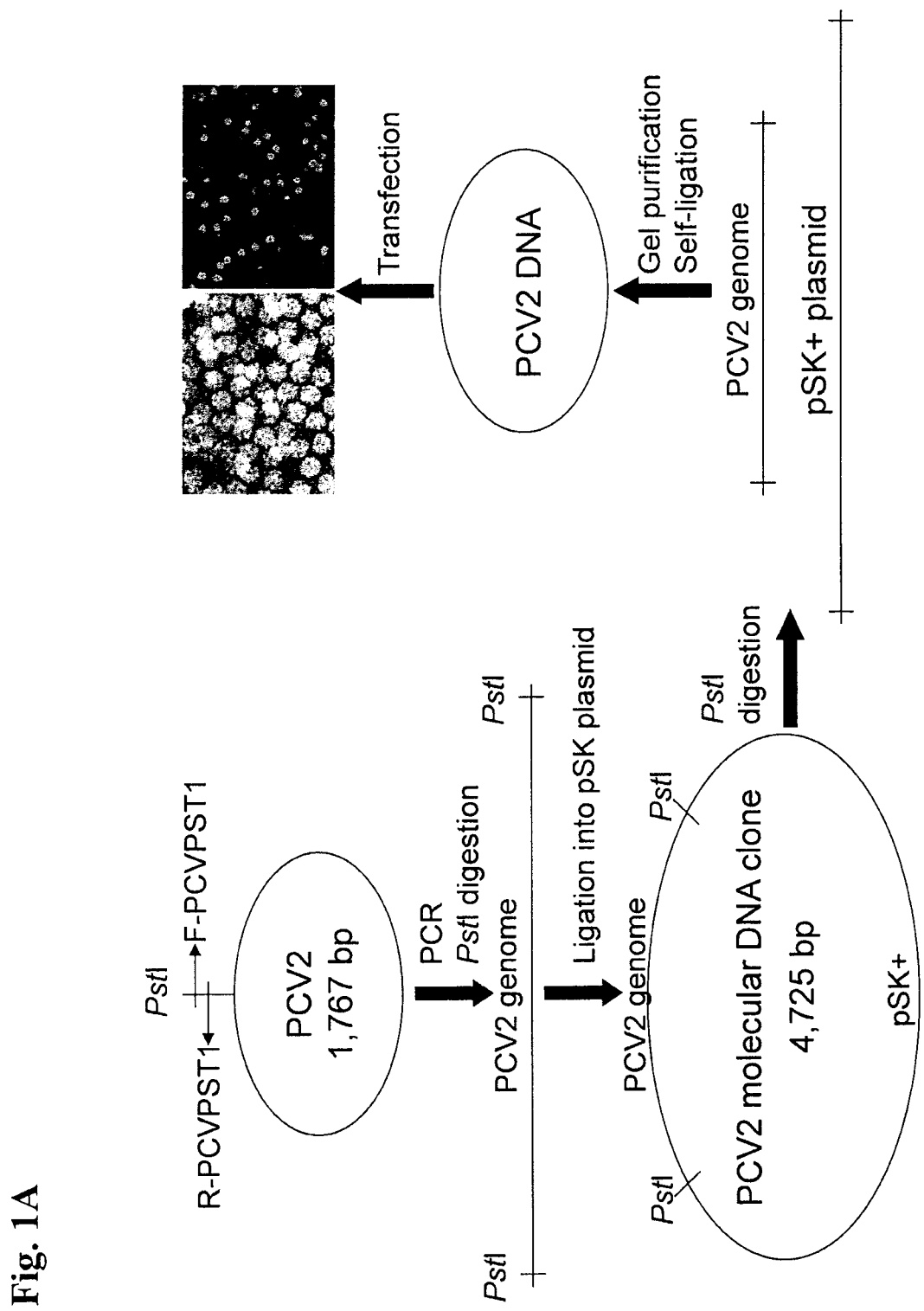
FIG. 1 (A) Construction of an infectious PCV2 molecular DNA clone. The relative positions of the primer pair used to amplify the complete PCV2 genome are indicated by the arrows (reverse primer, R-PCVPST1; forward primer, F—PCVPST1). The PCV2 genomic DNA amplified by PCR was digested with the PstI restriction enzyme and purified. The purified and digested genomic DNA was ligated into the pSK vector, which was predigested with the PstI enzyme to produce a molecular PCV2 DNA clone. The DNA clone was further digested and gel purified for self-ligation of PCV2, then the circular PCV2 DNA was transfected into PK15 cells. (B) Illustration of the construct of PCV2 mutant lacking ORF3 gene. (C) Genetic map of PCV2 strain BJW (GenBank accession number AY847748). The coding sequences of three open reading frames are annotated with nt coordinates that indicate the nucleotide site of each respective gene. The ORF2 and ORF3 genes are transcribed leftward and the ORF1 is transcribed rightward. The PstI restriction enzyme site is also indicated. (D) Analysis of ORF3 gene in PCV2-infected cells by RT-PCR. RNA was isolated from PCV2- or mock-infected cells and reverse transcribed into cDNA. The cDNA was amplified with a pair of ORF3 primers. Positive fragment was amplified from PCV2 genome using PCR reaction. (E). Detection of ORF3 RNA by ISH from PCV2-infected PK15 cells. ORF3 mRNA expressions were detected in the nucleus of the infected cells at 24 (a), 48 (b), 72 (c), and 96 (d) h postinfection using antisense ORF3 DIG-labelled riboprobe. ORF1 mRNA expression was also detected in the infected cells at 48 h post-infection using sense ORF3 DIG-labelled riboprobe (e). No signals were detected in the mock-infected cells (f) using the antisense ORF3 riboprobe. Bars, 10 μm.

The present invention provides an immunogenic attenuated PCV2 virus wherein the attenuation is attributable at least in part to aberrant ORF3 expression.

The attenuated viruses of the present invention are immunogenic that is they are capable of eliciting an immune response. The attenuated viruses may be used in a vaccine composition as described below for eliciting a protective immune response against subsequent challenge by a wild-type PCV2 virus.

Whilst the viruses of the present invention are capable of eliciting an immune response and are infectious they are sufficiently attenuated so as to not to cause unacceptable symptoms of PMWS (or any other disease which may be caused by PCV2) in the immunized host. In one embodiment, the virus is sufficiently attenuated so that symptoms of infection will not occur in most immunized individuals.

The attenuation is attributable at least in part to aberrant ORF3 expression. Hence, the viruses of the present invention have a reduced or absent ability to induce apoptosis. In one embodiment, the attenuation is attributable wholly to aberrant ORF3 expression.

For the avoidance of doubt, the term "reduced" as used herein includes the term absent unless the context clearly indicates otherwise.

In one embodiment, the aberrant ORF3 expression is qualitative. Thus, the protein expressed from ORF3 may, for example, have reduced or absent function as compared with the wild type ORF3 protein.

By "reduced or absent function" we include where the ORF3 protein has one or more mutations which result in the encoded protein having reduced or absent ability to induce apoptosis as compared with the wild type ORF3 protein.

In one embodiment, the aberrant ORF3 expression is quantitative. Thus, there may be reduced or absent expression of protein from ORF3 as compared with wild-type, pathogenic PCV2.

In one embodiment, the aberrant ORF3 expression may be qualitative and quantitative, i.e. the ORF3 protein has reduced or absent function vis-à-vis the wild-type ORF3 protein and the amount of expression of the ORF3 protein is less than the expression of the ORF3 protein from the wild-type PCV2 viruses.

In one embodiment, there is a mutation in the ORF3 sequence.

In one embodiment, there is a double mutation in the ORF3 sequence.

In one embodiment, there is a triple mutation in the ORF3 sequence.

In one embodiment, there is a mutation in another region of the virus (i.e. in a region other than ORF3) which affects ORF3 expression.

The mutation(s) in the viruses of the invention should be such that viral replication still occurs.

In one embodiment the mutation is such that functional ORF1 is still produced, i.e. the protein encoded by ORF1 is still capable of fulfilling its replicative role. In one such embodiment, there is a mutation in the ORF3 sequence which is such that the mutation does not result in any change in the protein encoded by ORF1.

In one embodiment the start codon of ORF3 is mutated so that it is non-functional. The start codon ATG of ORF3 may, for example, be mutated so A is replaced by G, i.e. the start codon ATG is mutated to GTG. Such a mutation has the advantage that, by virtue of the degeneracy of the genetic code, it does not result in any change in the protein encoded by ORF1.

In one embodiment, a stop codon is substituted for alanine in ORF3 resulting in the production of a non-functional truncated 26 amino-acid ORF3 protein.

In one embodiment, substitutions are made to the amino acid sequence in ORF3 so that electrical charges of the selected amino acid in the alpha region of the protein are reversed or become neutral and thereby cause the resulting protein to unfold and become non-functional. In one mutant, Glutamine− is changed to Lysine+ at amino acid 61.

As described in the Examples section below such mutants was produced by introducing a specific mutation into the genome of a PCV2 clone, using the QuickChange Site-Directed Mutagenesis Kit (Stratagene). Mutant plasmid was generated with a set of mutagenesis primers (forward primer: 5'-GGGATGGTTACCACGGTGAAGTGGTTGTTA-3', reverse prime: TAACAACCACTTCTTCACCGTGGTAAC-CATCCC-3') according to the manufacturer's instructions. The mutation [(nt 671) indicated in bold letters in FIG. 1B] will not alter the amino acid sequence of ORF1 protein at the site, but will stop the expression of the ORF3 protein.

Examples of mutations which may be employed in the present invention include: the introduction of a stop codon; rearrangements; substitution mutations (e.g. mis-sense and nonsense mutations); deletion mutations (the deletion of one or more nucleotides or the deletion of one or more codons); frame shift mutations; and insertions (the insertion or one or more nucleotides or the insertion of one or more codons). Methods for the introduction of mutations are well known in the art and can be readily accomplished by the skilled person. For example, site-directed mutagenesis is able to add, delete or change one or more nucleotides.

The effect of a mutation on ORF3 function/expression may, for example, be determined using the apoptosis assay described in the Materials and Methods section below.

In one embodiment, the mutation is, with respect to the ORF1 protein, a silent mutation (i.e. a mutation which does not have a significant deleterious effect on ORF1 function and in one embodiment has no effect on ORF1 function).

In addition to there being one or more mutations in the virus which result in aberrant ORF3 function, there may optionally be one or more further mutations in the virus. The mutation may, for example, be a mutation of any of the types described above such as a deletion mutation.

In one embodiment, the virus does not comprise any changes in its genome which impair its ability to induce an immune response against PCV2.

In one embodiment, the virus does not comprise any changes in the ORF2 sequence which result in a change of the encoded ORF2 protein.

In one embodiment, the virus does not comprise any changes in the ORF1 sequence which result in a change of the encoded ORF1 protein.

In one embodiment of the invention, the PCV2 virus does not differ, or substantially differ, from a wild type (pathogenic) PCV2 virus except for the introduction of one or more mutations in the virus which cause aberrant ORF3 expression.

The PCV2 viruses of the invention are in one embodiment provided in an isolated form. By isolated is meant to refer to PCV2 which is in other than a native environment of a wild-type virus. For example, the virus may be a component of a cell culture or other artificial medium where it can be propagated and characterized in a controlled setting; as a component or a cell culture supernatant; as a component of a pharmaceutical composition; or partially or completely purified from its native environment.

Whilst the above discussion pertains to the attenuated viruses of the invention, certain portions of the above also pertains to other aspects of the invention where appropriate, such as the nucleic acid molecules of the invention (see below).

Vaccines

The present invention provides vaccines comprising viruses of the present invention. Such compositions can be prepared in accordance with standard techniques well known to those skilled in the veterinary or pharmaceutical arts.

The vaccines of the invention comprise an immunologically effective amount of the virus. As a result of the vaccination with an immunogenically effective amount of PCV2 produced as described herein, the subject becomes at least partially or completely immune to PCV2 infection, or resistant to developing moderate or severe PCV2 infection. The viruses of the present invention may be used to elicit a humoral and cellular response.

Preferably, the subject is protected to an extent in which one to all of the adverse physiological symptoms or effects of the PMWS are significantly reduced, ameliorated or totally prevented.

In practice, the exact amount required for an immunologically effective dose may vary from subject to subject depending on factors such as the age and general condition of the subject, the nature of the formulation and the mode of administration and so forth. Thus, it is not possible to specify an exact "effective amount". However, for any given case, an appropriate "effective amount" may be determined by one of ordinary skill in the art using only routine experimentation.

For instance, methods are known in the art for determining or titrating suitable dosages of active antigenic agent to find minimal effective dosages based on the weight of the pig, concentration of the antigen and other typical factors. The dosage of the composition(s), concentration of components therein and timing of administering the composition(s), which elicit a suitable immunologic response, can be determined by methods such as by antibody titrations of sera, e.g., by ELISA and/or seroneutralization assay analysis and/or by vaccination challenge evaluation in pig.

The vaccines of the invention may comprise a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to the subject. Useful carriers are well known in the art, and include, e.g., water, buffered w water, 0.4% saline, 0.3% glycine, hyaluronic acid and the like.

In one embodiment of the invention the vaccine comprises an adjuvant. The adjuvant is a substance that increases the immunological response of the subject (e.g. pig) to the vaccine. Suitable adjuvants include, but are not limited to, aluminum hydroxide (alum), immunostimulating complexes (ISCOMS), non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

In one embodiment, there is provided a vaccine which additionally comprises at least one immunogen from at least one additional pathogen, e.g. a pig pathogen such as Porcine Reproductive and Respiratory Syndrome (PRRS), *Mycoplasma hyopneumoniae, Actinobacillus pleuropneumoniae, E. coli, Bordetella bronchiseptica, Pasteurella multocida, Erysipelothrix rhusiopathiae,* Pseudorabies, Hog cholera, Swine Influenza, and Porcine Parvovirus (PPV). The immunogen from the additional pathogen may be included within the genome of the viruses of the invention or may be present as a separate moiety within the vaccine compositions of the invention.

The PCV2 produced in accordance with the present invention can be combined with viruses of other PCV2 strains etc. Alternatively, protective epitopes of multiple types may be engineered into one virus. Such techniques are well known in the art and can be readily be achieved by the skilled artisan.

The vaccines of the invention can conveniently be administered intranasally, transdermally (i.e., applied on or at the skin surface for systemic absorption), parenterally, etc. The parenteral route of administration includes, but is not limited to, intramuscular, intravenous, intraperitoneal, intradermal (i.e., injected or otherwise placed under the skin) routes and the like.

The vaccines of the invention may be adapted for administration by any one of the aforementioned routes.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Examples of pharmaceutically acceptable carriers, excipients or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Typically, the vaccines of the present invention will comprise a suspension of the virus and a stabilizer.

The vaccines of the invention can be administered as single doses or in repeated doses.

The vaccines of the invention can be administered alone, or can be administered simultaneously (i.e. at the same time as) or sequentially administered (i.e. at different times) with one or more further compositions (e.g., other porcine immunogenic or vaccine compositions). Where the compositions are administered at different times (i.e. sequentially) the administrations may be separate from one another or overlapping in time.

In one embodiment of the invention the subject is immunized using a single dose of the virus of the invention.

In one embodiment, the vaccine compositions containing the PCV2 of the invention are administered to a subject susceptible to or otherwise at risk for PCV2 infection to enhance the subject's own immune response capabilities.

The subject to which the vaccine is administered is in one embodiment a pig. However, the subject may be any animal (e.g. mammal) in which it may be desirable to elicit an immune response to the virus in. The animal may be susceptible to infection by PCV2 or a closely related virus.

Whilst it is generally envisaged that the subject is a pig, it may be desirable to administer a vaccine of the invention to other types of animals. For instance, "test" animals may be administered a vaccine of the invention in order to evaluate the performance of the vaccine with a view to eventual use or development of a vaccine for pigs.

Desirably, the vaccine is administered to a subject which has not yet been exposed to the PCV2 virus.

In one embodiment the subject is a pig which is in need of vaccination against Postweaning Multisystemic Wasting Syndrome (PMWS).

It is envisaged that the vaccines may be useful for not only administration to adult pigs, but also to young pigs or to pregnant females. The vaccination of the latter makes it possible to confer passive immunity to the newborns (maternal antibodies). In one embodiment the pig is less than 7, 6, 5, 4, 3, 2 or 1 week old.

In one embodiment, the pig is 1 to 6 weeks old; 2 to 5 weeks old; or 3 to 4 weeks old.

Production of the Viruses

One aspect of the invention provides a host cell for production of attenuated PCV2 of the invention.

A wide variety of host cells may be useful for the production of the viruses of the invention and include porcine cells such as porcine kidney cells, e.g. PK15 cells.

The invention also provides a method for producing attenuated PCV2 of the invention, the method comprising growing a host cell of the invention under suitable conditions in a manner allowing production of the attenuated PCV2. The method may further comprise isolating the attenuated PCV2 from the culture medium and optionally further processing the attenuated PCV2.

Suitable growth conditions for the host cell will be known to those skilled in the art or can be readily determined by those skilled in the art and will include the selection of, inter alia, suitable nutrient conditions. In one embodiment, the culture medium comprises at least water, salts, nutrients, essential amino acids, vitamins and antibiotics, and may also include one or more growth factors.

Proteins Capable of Inducing Apoptosis

A tenth aspect of the invention provides a protein capable of inducing apoptosis.

In one embodiment, the protein comprises the amino acid sequence as set forth in SEQ ID NO.1:

```
MVTIPPLVSRWFPVCGFRVCKISSPFAFTTTRWPHNDVYIRLPITLLHFP

AHFQKFSQPAEISDKRYRVLLCNGHQTPALQQGTHSSRQVTPLSLRSRSS

TFYQ
```

In one embodiment there is provided a protein which consists of the amino acid sequence as set forth in SEQ ID NO. 1.

The proteins of the invention include functional equivalents, variants, active fragments and fusion proteins of those proteins which comprise or consist of the amino acid sequence set forth in SEQ ID NO:1. For the avoidance of doubt, the following are included within the scope of the invention: functional equivalents of the active fragments and fusion proteins; active fragments of the functional equivalents and fusion proteins; and fusion proteins comprising a functional equivalent or active fragment.

The term "fragment" refers to a nucleic acid or polypeptide sequence that encodes a constituent or is a constituent of full-length protein. In terms of the polypeptide the fragment possesses qualitative biological activity in common with the full-length protein. A biologically active fragment of used in accordance with the present invention may typically possess at least about 50% of the activity of the corresponding full length protein, more typically at least about 60% of such activity, more typically at least about 70% of such activity, more typically at least about 80% of such activity, more typically at least about 90% of such activity, and more typically at least about 95% of such activity.

The term "variant" as used herein refers to substantially similar molecules. Generally, nucleic acid sequence variants encode polypeptides which possess qualitative biological activity in common. Generally, polypeptide sequence variants also possess qualitative biological activity in common. Further, these polypeptide sequence variants may share at least 50%, 55%, 60%, 65%, 70%, 75%, 80%, 82%, 85%, 90%, 95%, 96%, 97%, 98% or 99% sequence identity.

The functional equivalents, active fragments and fusion proteins of the eighth aspect of the invention retain the ability of the wild type ORF3 protein (SEQ ID NO:1) to induce apoptosis. Apoptotic activity can, for example, be assessed using the apoptosis assay described in the Materials and Methods section below. Persons skilled the art will, however, be able to devise alternative or additional assays or means for assessing apoptotic activity.

In one embodiment of the invention there is provided a functional equivalent of SEQ ID NO.1 that contains, for example, single or multiple amino-acid substitution(s), addition(s), insertion(s) and/or deletion(s) and/or substitutions of chemically-modified amino acids. However, as mentioned above, such functional equivalents will retain the ability to induce apoptosis.

A functionally-equivalent protein according to this aspect of the invention includes proteins which have at least 65% sequence identity to the amino acid sequence set forth in SEQ ID NO.1.

Methods of measuring protein sequence identity are well known in the art and it will be understood by those of skill in the art that in the present context, sequence identity is calculated on the basis of amino acid identity (sometimes referred to as "hard homology"). For example the UWGCG Package provides the BESTFIT program which can be used to calculate sequence identity (for example used on its default settings) (Devereux et al (1984) Nucleic Acids Research 12, p 387-395). The PILEUP and BLAST algorithms can be used to calculate sequence identity or line up sequences (typically on their default settings), for example as described in Altschul S. F. (1993) J Mol Evol 36:290-300; Altschul, S, F et al (1990) J Mol Biol 215:403 Software for performing BLAST analyses is publicly available through the National Center for Biotechnology Information on the world wide web through the internet at, for example, "www.ncbi.nlm.nih.gov/". This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the both strands. The BLAST algorithm performs a statistical analysis of the similarity between two sequences; see e.g., Karlin and Altschul (1993) Proc. Nad. Acad. Sci. USA 90: 5873 One measure of similarity provided by the BLAST algorithm is the smallest sum probability (P(N)), which provides an indication of the probability by which a match between two nucleotide or amino acid sequences substituted for each other.

In one embodiment, a functionally equivalent protein according to this aspect of the invention exhibits a degree of sequence identity with the protein set forth in SEQ ID NO.1, or with a fragment thereof, of greater than 65%. The proteins may have a degree of sequence identity of at least 70%, 80%, 85%, 90%, 95%, 97%, 98% or 99%.

Functionally-equivalent proteins according to the invention are therefore intended to include mutants (such as mutants containing amino acid substitutions, insertions or deletions). Such mutants may include proteins in which one or more of the amino acid residues are substituted with a conserved or non-conserved amino acid residue (preferably a conserved amino acid residue) and such substituted amino acid residue(s) may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr.

Particularly preferred are proteins in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. "Mutant" proteins also include proteins in which one or more of the amino acid residues include a substituent group.

Also included within the scope of the invention are active fragments wherein "active fragment" denotes a truncated protein that retains the ability of the wild type ORF3 protein (SEQ ID NO.1) to induce apoptosis.

Active fragments of the invention should comprise at least n consecutive amino acids from a protein of the invention (e.g. from SEQ ID NO. 1 or a functional equivalent thereof). n typically is 50, 75, 85, 90, 95 or 100 or more.

In one embodiment, the active fragment comprises at least 70%, 75%, 80%, 85%, 90%, 95%, 97% or 99% of the sequence of SEQ ID NO. 1 or a functional equivalent thereof.

Such fragments may be "free-standing", i.e. not part of or fused to other amino acids or proteins, or they may be comprised within a larger protein of which they form a part or region. When comprised within a larger protein, the fragment of the invention in one embodiment forms a single continuous region. Additionally, several fragments may be comprised within a single larger protein.

In one embodiment of the invention there is provided a fusion protein comprising a protein of the invention fused to a peptide or other protein, such as a label, which may be, for instance, bioactive, radioactive, enzymatic or fluorescent, or an antibody.

For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature protein may be fused with another compound, such as a compound to increase the half-life of the protein (for example, polyethylene glycol).

Nucleic Acid Molecules Encoding Proteins of the Tenth Aspect of the Invention

An eleventh aspect of the invention provides a nucleic acid molecule which encodes a protein of the tenth aspect of the invention.

In one embodiment, the nucleic acid molecule comprises the sequence set forth in SEQ ID NO. 2.

In one embodiment, the nucleic acid molecule consists of the sequence as set forth in SEQ ID NO. 2.

It will be appreciated by those skilled in the art that as a result of the degeneracy of the genetic code, a multitude of nucleic acid molecules encoding the proteins of the eighth aspect of the invention, some bearing minimal sequence identity to SEQ ID NO.2, may be produced. Thus, the invention contemplates each and every possible variation of polynucleotide sequence that could be made by selecting combinations based on possible codon choices.

In one embodiment of the invention there is provided a nucleic acid molecule which comprises a degenerate version of SEQ ID NO.2, i.e. the nucleic acid molecule comprises a nucleic acid sequence in which one or more codons of SEQ ID NO.2 are replaced with a degenerate codon which codon codes for the same amino acid as the native codon of SEQ ID NO.2.

The nucleic acid molecules of the present invention may, for example, be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The term "nucleic acid molecule" (and analogous expressions such as "nucleic acids", "nucleic acid sequences" etc.) also includes analogues of DNA and RNA, such as those containing modified backbones.

Typically, the nucleic acid molecules of the invention also includes within its scope a functional equivalent or fragment of the nucleic acid sequence, wherein said functional equivalent or fragment encodes a protein which retains the ability of the wild type ORF3 protein to induce apoptosis. Such functional equivalents and fragments can be located and isolated using standard techniques in molecular biology, without undue trial and experimentation.

The functional equivalents may be homologous to SEQ ID NO. 2, or to a sequence corresponding thereto within the degeneration of the genetic code, while still encoding a protein which retains the ability to induce apoptosis. In one embodiment of the invention, the nucleic acid molecule comprises a sequence having a homology of at least 70%, 80%, 85%, 90%, 92%, 95%, 97%, 98%, or 99% to the nucleotide sequence according to SEQ ID NO:2, or to a sequence corresponding thereto within the degeneration of the genetic code, while still encoding a protein which retains the ability to induce apoptosis.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), *Journal of Molecular Biology*, 48, 443-453). Using GAP with the following settings for DNA sequence comparison: GAP creation penalty of 5.0 and GAP extension penalty of 0.3.

Nucleic acid molecules may be aligned to each other using the Pileup alignment software, available as part of the GCG program package, using, for instance, the default settings of gap creation penalty of 5 and gap width penalty of 0.3.

The nucleic acid molecules of the invention may also include within its scope a functional equivalent capable of hybridising to the nucleic acid sequence defined in SEQ ID NO.2, or to a sequence corresponding thereto within the degeneration of the genetic code, under conditions of low stringency, more preferably, medium stringency and still more preferably, high stringency. Low stringency hybridisation conditions may correspond to hybridisation performed at 50° C. in 2×SSC.

Suitable experimental conditions for determining whether a given nucleic acid molecule hybridises to a specified nucleic acid may involve presoaking of a filter containing a relevant sample of the nucleic acid to be examined in 5×SSC for 10 min, and prehybridisation of the filter in a solution of 5×SSC, 5×Denhardt's solution, 0.5% SDS and 100 µg/ml of denatured sonicated salmon sperm DNA, is followed by hybridisation in the same solution containing a concentration of 10 ng/ml of a $^{32}$P-dCTP-labeled probe for 12 hours at approximately 45° C., in accordance with the hybridisation methods as described in Sambrook et al. (1989; Molecular Cloning, A Laboratory Manual, 2nd edition, Cold Spring Harbour, N.Y.).

The filter is then washed twice for 30 minutes in 2×SSC, 0.5% SDS at least 55° C. (low stringency), at least 60° C. (medium stringency), at least 65° C. (medium/high stringency), at least 70° C. (high stringency), or at least 75° C. (very high stringency). Hybridisation may be detected by exposure of the filter to an x-ray film.

Further, there are numerous conditions and factors, well known to those skilled in the art, which may be employed to alter the stringency of hybridisation. For instance, the length and nature (DNA, RNA, base composition) of the nucleic acid to be hybridised to a specified nucleic acid; concentration of salts and other components, such as the presence or absence of formamide, dextran sulfate, polyethylene glycol etc; and altering the temperature of the hybridisation and/or washing steps.

Further, it is also possible to theoretically predict whether or not two given nucleic acid sequences will hybridise under certain specified conditions. Accordingly, as an alternative to the empirical method described above, the determination as to whether a variant nucleic acid sequence will hybridise to the nucleic acid molecule defined in SEQ ID NO:2, or to a sequence corresponding thereto within the degeneration of the genetic code, can be based on a theoretical calculation of the $T_m$ (melting temperature) at which two heterologous nucleic acid sequences with known sequences will hybridise under specified conditions, such as salt concentration and temperature.

In determining the melting temperature for heterologous nucleic acid sequences ($T_{m(hetero)}$) it is necessary first to determine the melting temperature ($T_{m(homo)}$) for homologous nucleic acid sequence. The melting temperature ($T_{m(homo)}$) between two fully complementary nucleic acid strands (homoduplex formation) may be determined in accordance with the following formula, as outlined in Current Protocols in Molecular Biology, John Wiley and Sons, 1995, as:

$$T_{m(homo)}=81.5° C.+16.6(\log M)+0.41(\% GC)-0.61(\% \text{form})-500/L$$

M=denotes the molarity of monovalent cations,
% GC=% guanine (G) and cytosine (C) of total number of bases in the sequence,
% form=% formamide in the hybridisation buffer, and
L=the length of the nucleic acid sequence.

$T_m$ determined by the above formula is the $T_m$ of a homoduplex formation ($T_{m(homo)}$) between two fully complementary nucleic acid sequences. In order to adapt the $T_m$ value to that of two heterologous nucleic acid sequences, it is assumed that a 1% difference in nucleotide sequence between two heterologous sequences equals a 1° C. decrease in $T_m$. Therefore, the $T_{m(hetero)}$ for the heteroduplex formation is obtained through subtracting the homology % difference between the analogous sequence in question and the nucleotide probe described above from the $T_{m(homo)}$.

Mutated Nucleic Acid Molecules

A twelfth aspect of the invention provides a nucleic acid molecule comprising a mutated version of the nucleic acid molecule according to the eleventh aspect of the invention, the nucleic acid molecule being mutated such that there is aberrant expression of the protein encoded by the nucleic acid molecule of the ninth aspect of the invention.

With regard to this aspect of the invention, reference is made to the relevant portions of the above section entitled "The Attenuated Virus". However, it should be emphasised that the nucleic acid molecules of the twelfth aspect of the invention may not only be provided in the form of a virus, but may be provided in other forms, e.g. as nucleic acid molecules per se, vectors etc. and the relevant portions of the section entitled "The Attenuated Virus" accordingly apply mutatis mutandis to the provision of the nucleic acid molecules of the twelfth aspect of the invention in forms other than viruses.

By "aberrant expression of the protein encoded by the nucleic acid molecule of the ninth aspect of the invention" it should be appreciated that this includes: (i) the situation where reduced or absent protein is expressed from the mutated nucleic acid molecule (vis-à-vis the nucleic acid molecule of the eleventh aspect of the invention); and (ii) where the protein expressed by the mutated nucleic acid molecule has reduced or absent apoptotic function (vis-à-vis the protein encoded by the nucleic acid molecule of the eleventh aspect of the invention).

In one embodiment, ORF3 may comprise a mutation which results in reduced or absent expression of the ORF3 protein (e.g. due to a point mutation in the start codon of ORF3) or there may be a mutation which results in the resulting ORF3 protein having reduced or absent function, i.e. the encoded protein has a reduced ability to induce apoptosis (and in one embodiment cannot induce apoptosis).

In one embodiment of the twelfth aspect of the invention there is provided a nucleic acid sequence comprising or consisting of SEQ ID NO.3: GTGGTAACCATCCCACCACT-TGTTTCTAGGTGGTTTCCAGTATGTGGTTTC CGGGTCTGCAAAATTAGCAGC-CCATTTGCTTTTACCACAACCAGGTGGCCC CACAATGACGTGTACATTCGTCTTC-CAATCACGCTTCTGCATTTTCCCGCT CACTTTCAAAAGTTCAGCCAGCCCGCG-GAAATTTCTGACAAACGTTACAG GGTGCTGCTCTG-CAACGGTCACCAGACTCCCGCTCTCCAA-CAAGGTACTC ACAGCAGTAGACAGGTCACTCCGTTGTC-CTTGAGATCTAGGAGCTCCACA TTCTATCAGTAA, or a degenerate version thereof. This sequence, represents the ORF3 mutant sequence with a point mutation in the start codon so that no ORF3 protein is expressed.

In another embodiment of the twelfth aspect of the invention there is provided a nucleic acid sequence comprising or consisting of SEQ ID NO.19:
ATGGTAACCATCCCACCACT-TGTTTCTAGGTGGTTTCCAGTATGTGGT TTC-CGGGTCTGCAAAATTAGCAGC-CCATTTtgaTTTACCACAACCAGGTGGC CCCACAATGACGTGTACATTCGTCTTC-CAATCACGCTTCTGCATTTTCCCG CTCACTTTCAAAAGTTCAGCCAGC-CCGCGGAAATTTCTGACAAACGTTAC AGGGTGCT-GCTCTGCAACGGTCACCAGACTC-CCGCTCTCCAACAAGGTAC TCACAGCAGTAGACAGGTCACTCCGT-TGTCCTTGAGATCTAGGAGCTCCA CATTCTATCAG-TAA, or a degenerate version thereof. This sequence, represents the ORF3 mutant sequence with a point mutation inserting a stop codon at position 27 in the amino acid sequence so that the ORF3 protein is expressed in a truncated form.

In another embodiment of the twelfth aspect of the invention there is provided a nucleic acid sequence comprising or consisting of SEQ ID NO.21:

ATGGTAACCATCCCACCACT-TGTTTCTAGGTGGTTTCCAGTATGTGGT TTC-CGGGTCTGCAAAATTAGCAGC-CCATTTGCTTTTACCACAACCAGGTGG CCCCACAATGACGTGTACATTCGTCTTC-CAATCACGCTTCTGCATTTTCCC GCT-CACTTTCAAAAGTTCAGCCAGCCCGC-GaAAATTTCTGACAAACGTTAC AGGGTGCTGCTCTGCAACGGTCACCA-GACTCCCGCTCTCCAACAAGGTAC TCACAGCAGTA-GACAGGTCACTCCGTTGTCCT-TGAGATCTAGGAGCTCCA CATTCTATCAGTAA, or a degenerate version thereof. This sequence, represents the ORF3 mutant sequence with a point mutation such that the amino acid Glu− was changed to Lys+ so that the conformation of the secondary structure of the ORF3 protein is affected.

Proteins Encoded by the Mutated Nucleic Acid Molecules of the Invention

It will be appreciated from the foregoing that in some instances no protein will be encoded by a nucleic acid molecule of the twelfth aspect of the invention. However, where a protein is encoded by a nucleic acid molecule of the twelfth aspect of the invention such proteins are provided as a further aspect of the invention. Such proteins may be expressed at a lower level than the protein encoded by the wild-type nucleic acid sequence (SEQ ID NO.2) or will be a protein which has a reduced or absent function (in terms of its ability to induce apoptosis) vis-à-vis that of the wild-type protein (SEQ ID NO.1).

Provision of the Nucleic Acid Molecules in Various Forms

The nucleic acid molecules of the invention may be provided in various forms. They may be provided in the form of a nucleic acid molecule per se ("naked" nucleic acid molecules"); a vector; virus or host cell etc.

Vectors include expression vectors that contain a nucleic acid molecule of the invention. The vectors of the present invention may, for example, comprise a transcription promoter, and a transcription terminator, wherein the promoter is operably linked with the nucleic acid molecule, and wherein the nucleic acid molecule is operably linked with the transcription terminator.

In one embodiment there is provided a host cell transformed with a nucleic acid molecule according to the eleventh or twelfth aspect of the invention. Suitable examples of host cells will be known to those skilled in the art or can be readily selected by those skilled in the art. Host cells may, for example, include eukaryotic and prokaryotic cells. Examples of eukaryotic cells include mammalian (e.g. pig), fungal (e.g. *Saccharomyces cerevisiae*), insect and plant cells. Prokaryotic cells include, for example, *E. coli*.

The nucleic acid molecules of the invention (including the various moieties which may comprise them e.g. vectors, viruses, host cells) may be utilised for the production of a protein of the invention. Thus, for example, the invention provides a method of producing a protein of the invention, the method comprising culturing a host cell of the invention under conditions suitable for the expression of a protein of is the invention.

In an alternative embodiment, a protein of the invention may be produced by chemical synthesis of the protein. Chemical synthesis may be achieved by, for example, solid-phase peptide synthesis. Such techniques are well known in the art and will be readily able to be carried out by the skilled person.

The production of a protein of the invention may be followed by the purification of the protein. Methods for the purification of proteins are well known in the art and can be readily performed by the skilled person.

Antibodies and Methods for Generating Antibodies

A fifteenth aspect of the invention provides an antibody capable of binding to protein of the tenth or thirteenth aspect of the invention.

A sixteenth aspect of the invention provides a method of generating an antibody which is capable of binding to a protein of the tenth or thirteenth aspect of the invention. The method may comprise immunizing an animal (e.g. rabbit, guinea pig, rodent etc.) with a protein of the tenth or thirteenth aspect of the invention and harvesting the antibody produced thereby.

In one embodiment of the fifteenth and sixteenth aspects of the invention the antibody is capable of binding to an amino acid sequence comprised in the sequence set forth in SEQ ID NO. 1.

The antibodies of the invention may be polyclonal or monoclonal antibody preparations, monospecific antisera, human antibodies, or may be hybrid or chimeric antibodies, such as humanized antibodies, altered antibodies (Fab')$_2$ fragments, F(ab) fragments, Fv fragments, single-domain antibodies, dimeric or trimeric antibody fragments or constructs, minibodies, or functional fragments thereof which bind to the antigen in question.

Antibodies may be produced using techniques well known to those of skill in the art and disclosed in, for example, U.S. Pat. Nos. 4,011,308; 4,722,890; 4,016,043; 3,876,504; 3,770,380; and 4,372,745. See also Antibodies—A Laboratory Manual, Harlow and Lane, eds., Cold Spring Harbor Laboratory, N.Y. (1988). For example, polyclonal antibodies are generated by immunizing a suitable animal, such as a mouse, rat, rabbit, sheep, or goat, with an antigen of interest. In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2-6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler & Milstein (1975) Nature 256:495-497, or a modification thereof. Typically, a mouse or rat is immunized as described above. Rabbits may also be used. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

Humanized and chimeric antibodies are also useful in the invention. Hybrid (chimeric) antibody molecules are generally discussed in Winter et al. (1991) Nature 349: 293-299 and U.S. Pat. No. 4,816,567. Humanized antibody molecules are generally discussed in Riechmann et al. (1988) Nature 332: 323-327; Verhoeyan et al. (1988) Science 239:1534-1536; and U.K. Patent Publication No. GB 2,276,169, published 21 Sep. 1994).

An antibody is said to be "capable of binding" a molecule if it is capable of specifically reacting with the molecule to thereby bind the molecule to the antibody.

In one embodiment, the antibody or fragment thereof has binding affinity or avidity greater than about $10^5$ $M^{-1}$, more preferably greater than about $10^6$ $M^{-1}$, more preferably still greater than about $10^7$ $M^{-1}$ and most preferably greater than about $10^8$ $M^{-1}$ or $10^9$ $M^{-1}$. The binding affinity of an antibody can be readily determined by one of ordinary skill in the art, for example, by Scatchard analysis (Scatchard, Ann. NY Acad. Sci. 51:660 (1949)).

Provision of the Moieties of the Invention in Isolated Form

The proteins, nucleic acid molecules and antibodies of the present invention may be "isolated". The term isolated as used herein means altered "by the hand of man" from its natural state; i.e., if it occurs in nature, it has been changed or it has been removed from its natural host or environment. Associated impurities may be reduced or eliminated.

The various moieties of the invention may, for example, be provided in the form of a pharmaceutical composition such as a vaccine formulation. Thus, in one aspect of the invention there is provided a pharmaceutical composition comprising a nucleic acid molecule, protein, antibody, antagonist, agonist, virus, vector or host cell of the invention.

With regard to the pharmaceutical compositions and vaccines, the reader is referred to the relevant portions of the above description.

Screening for Agonists or Antagonists

The present invention provides methods for screening for agonists or antagonists of the proteins of the invention. Such agonists and antagonists may have various utilities. For examples, antagonists of the ORF3 protein may find utility in the treatment of PMWS as such antagonists would reduce the ability of the ORF3 protein to induce apoptosis and hence the pathogenicity and symptoms of PCV2 could be reduced.

The proteins of the invention can be used to screen libraries of compounds in any of a variety of drug screening techniques. Such compounds may modulate (agonise or antagonise) the activity of a protein of the invention (e.g. a protein according to the tenth or thirteenth aspects of the invention).

In one embodiment, the method comprises contacting a test compound with a protein of the invention and determining if the test compound binds to the protein of the invention. The method may further comprise determining if the test compound is enhances or decreases the activity of the protein (i.e. its ability to induce apoptosis) of the invention.

Methods for determining if the test compound enhances or decreases the activity of a protein of the invention will be known to persons skilled in the art and include, for example, docking experiments/software or X ray crystallography.

The protein of the invention that is employed in the screening methods of the invention may be free in solution, affixed to a solid support, borne on a cell surface or located intracellularly.

Test compounds (ie potential agonist or antagonist compounds) may come in various forms, including natural or modified substrates, enzymes, receptors, small organic molecules such as small natural or synthetic organic molecules of up to 2000 Da, preferably 800 Da or less, peptidomimetics, inorganic molecules, peptides, proteins, antibodies, structural or functional mimetics of the aforementioned.

A further method for identifying antagonists or agonists of the ORF3 protein may comprise expressing in a cell a protein of the tenth aspect of the invention which is capable of inducing apoptosis and exposing the cell to the test compound and determining if the test compound affects the ability of the protein to induce apoptosis and to thereby determine if the test compound exhibits antagonistic or agonistic activity.

Test compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in immunology 1(2):Chapter 5 (1991).

Compounds that are most likely to be good antagonists or agonists are molecules that bind to the protein of the invention (in the case of antagonists without inducing the biological effects of the protein upon binding to it).

Antagonists may alternatively function by virtue of competitive binding to a receptor for a protein of the invention.

Agonists may alternatively function by binding to a receptor for a protein of the invention and increasing the affinity of the binding between the receptor and the protein of the invention.

Potential antagonists include small organic molecules, peptides, proteins and antibodies that bind to the protein of the invention and thereby inhibit or extinguish its activity. In this fashion, binding of the protein to normal cellular binding molecules may be inhibited, such that the natural biological activity of the protein is prevented.

In certain of the embodiments described above, simple binding assays may be used, in which the adherence of a test compound to a surface bearing the protein is detected by means of a label directly or indirectly associated with the test compound or in an assay involving competition with a labelled competitor.

Another technique for drug screening which may be used provides for high throughput screening of compounds having suitable binding affinity to the protein (see WO84/03564). In this method, large numbers of different small test compounds are synthesised on a solid substrate, which may then be reacted with the protein and washed. One way of immobilising the protein is to use non-neutralising antibodies. Bound protein may then be detected using methods that are well known in the art. Purified protein can also be coated directly onto plates for use in the aforementioned drug screening techniques.

In silico methods may also be used to identify agonist and antagonists. The activity of the agonist and antagonist moeities may then be confirmed, if desired, experimentally.

A further aspect of the invention provides an agonist or antagonist identified by a screening method of the invention.

Whilst the invention has in certain places been described in relation to particular aspects of the invention the skilled reader will appreciate that the comments may apply equally to other aspects of the invention and the description should be construed accordingly.

In accordance with the present invention there may be employed conventional molecular biology, microbiology, immunology, and recombinant DNA techniques within the skill of the art.

Such techniques are explained fully in the literature. See, e.g., Sambrook et al, "Molecular Cloning: A Laboratory Manual" ($3^{rd}$ edition, 2001); "Current Protocols in Molecular Biology" Volumes I-III [Ausubel, R. M., ed. (1999 and updated bimonthly)]; "Cell Biology: A Laboratory Handbook" Volumes I-III [J. E. Celis, ed. (1994)]; "Current Protocols in Immunology" Volumes I-IV [Coligan, J. E., ed. (1999 and updated bimonthly)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Culture of Animal Cells, 4th edition" [R. I. Freshney, ed. (2000)]; "Immobilized Cells And Enzymes" [IRL Press, (1986)]; B. Perbal, "A Practical Guide To Molecular Cloning" (1988); Using Antibodies: A Laboratory Manual: Portable Protocol No. I, Harlow, Ed and Lane, David (Cold Spring Harbor Press, 1998); Using Antibodies: A Laboratory Manual, Harlow, Ed and Lane, David (Cold Spring Harbor Press, 1999).

EXAMPLES

The following is provided to illustrate embodiments of the invention and should not be viewed as limiting the scope of the invention.

The inventors have discovered a novel viral gene, ORF3, during productive infection of PCV2 in PK15 cells. The results of infection with ORF3-deficient PCV2 by site-directed mutagenesis indicated that the protein is not essential for viral replication.

Transfection of cells with the ORF3 alone induced apoptosis using a pathway similar to that described in the context of viral infection. This is further confirmed by a significant decrease in apoptotic activity of infected cells in the absence of the ORF3 expression, suggesting that the protein plays a major role in the induction of virus-induced apoptosis, and implicating that it may be involved in viral pathogenesis.

After infecting Balb/C mice with the mutant PCV2 lacking the ORF3 gene expression, no pathological changes were observed in the mice as compared to those infected with the wild type PCV2, hence suggesting the mutant PCV2 has a potential for being the attenuated live vaccine against PCV2 induced PMWS.

In this present invention, we used specific antibody against ORF3 to show that it is indeed expressed in PCV2-infected cells and is not essential for PCV2 replication in cultured cells. Moreover, the ORF3 protein has been shown to play a major role in PCV2-induced apoptosis using a pathway similar to that described in the context of viral infection. This is further confirmed by a significant decrease in apoptotic activity of infected cells in the absence of the ORF3 expression.

In this invention, the mutant PCV2 inoculum was administered to groups of experimental 8 week old mice, using healthy mice as a negative control, and PCV2 infected mice as a positive control. A single dose of $10^5$ $TCID_{50}$ (50% tissue cultured infectious dose) was injected into each of the experimental mice. The experimental set on one hand showed significant lesser degree of microscopic lesions and detrimental physical effects, while on the other hand, appear to have as abundant cytoplasmic labelling against the PCV2 antigen as the positive control.

Materials and Methods

Virus and Cells

The permanent PK15 cell line, which was free of PCV, was maintained in minimal essential medium (MEM, Gibco) supplemented with 5% heat-inactivated fetal bovine serum (FBS), 5% L-glutamine, 100 U/ml of penicillin G, and 100 µl/ml streptomycin at 37° C. in a humidified 5% $CO_2$ incubator. Cos-7 cells, used for transient expression assay, were maintained in Dulbecco's modified Eagle medium (DMEM, Gibco) supplemented with 10% FBS. The PCV2 virus strain BJW used in the study was originally isolated from a kidney tissue sample of a pig with naturally occurring PMWS in the Northern region of China. The kidney tissues were treated and inoculated to PK15 cells and its genome sequence has been deposited in GenBank (Accession Number: AY847748).

Raising Antibody to ORF3

As shown in FIG. 1A, the ORF1 and ORF2 as well as ORF3 genes are indicated in the genetic map of the PCV2 strain BJW. The DNA encoding ORF3 full length was cloned into PQE30 and transformed into *Escherichia coli* BL21 cells. These cells were induced to express ORF3 with IPTG (isopropyl-β-D-thiogalactopyranoside) and allowed to grow for 4 h at 37° C. His-tag fusion protein was purified, and the preparation was injected into mice to raise polyclonal antibody. After four injections, the mice were bled, and the sera were tested for reactivity to ORF3. The antibody showed specific reactivity to ORF3 expressed in PK15 cells infected with the PCV2 virus or transfected with an ORF3 expression construct.

Construction of PCV2 Mutant and Plasmids

A pair of PCR primers was designed according to the sequence of the PCV2 isolate strain BJW: forward primer F—PCVPST (5'-TGCACTGCAGTAAAGAAGGCAACT-TAC-3') and reverse primer R-PCVPST (5'-TGCACTG-CAGTATTCTTTATTCTGCTG-3'). This pair of primers amplifies the complete genome of PCV2 with an overlapping region containing the unique PstI restriction enzyme site (FIGS. 1A & C). Briefly, DNA was extracted using the QIAamp DNA Minikit (Qiagen) from a kidney tissue sample of a pig with naturally occurring PMWS. The extracted DNA was amplified by PCR (Perkin-Elmer) with the following conditions: initial enzyme activation step at 94° C. for 5 min, followed by 35 cycles of denaturation at 94° C. for 1 min, annealing at 48° C. for 1 min, extension at 72° C. for 2 min, and a final extension at 72° C. for 10 min. The PCR product of expected size was separated by gel electrophoresis and purified using PCR purification kit (Qiagen).

To construct a molecular DNA clone containing the PCV2 genome, the PCR product was cloned into the pBlueScript SK (pSK) vector. The clone was sequenced on both strands using the M13 forward and reverse universal primers as well as PCV2 genome-specific primers and the ABI Prism Dye terminator cycle sequencing kit (PE Biosystems).

Specific mutation was introduced into the cloned PCV2 genome using the QuickChange Site-Directed Mutagenesis Kit (Strategene). Mutant plasmid was generated with a set of mutagenesis primers (forward primer: 5'-GGGATGGTTAC-CACGGTGAAGTGGTTGTTA-3', reverse primer: TAA-CAACCACTTCTTCACCGTGGTAACCATCCC-3') according to the manufacturer's instructions. The mutation (nt 671) is indicated in italic bold letters (FIG. 1B) and cannot alter the amino acid sequence of ORF1 protein at the site. After the PCV2 genome was excised from the pSK plasmid and circularized by ligation, the ligated DNA mixture was transfected into approximately 60-80% confluent PK15 cells.

To prepare recombinant eukaryotic expression plasmids, the coding sequence of ORF1, ORF2, and ORF3 genes were amplified from PCV2 genome. The following primers: GFP-ORF1(5): 5'-CCGCTCGAGCTATGCCCAGCAAGAA-GAATGG-3' and GFP-ORF1(3): 5'-CGGGGTACCTCAG-TAATTTATTTCATATG-3', GFP-ORF2(5): 5'-CCCAAGCTTCGATGACGTACCCAAGGAGGCG-3' and GFP-ORF2(3): 5'-CGGGGTACCTTATGGTT-TAAGTGGGGGGTC-3', GFP-ORF3(5): 5'-CCCAAGCT-TCGATGGTAACCATCCCACCACTTG-3' and GFP-ORF3 (3): 5'-CGGGGTACCTTACTTATCGAGTGTGGAGCTC-3', were used to amplify these three genes, respectively. The XhoI/KpnI fragment ORF1 and HindIII/KpnI fragments ORF2 and ORF3, were directionally cloned into the corresponding sites of eukaryotic expression vector pEGFP-C1 (Clontech), downstream of the human cytomegalovirus (HCMV) promoter, to obtain GFP-ORF1, GFP-ORF2 and GFP-ORF3, respectively. They were sequenced to confirm that no errors were introduced as a result of PCR amplification.

Transfection and Infection

For genome transfections, PstI-digested PCV2 or ORF3-deficient PCV2 for generating recombinant PCV2 (rPCV2) or mutant PCV2 (rPCV2ORF3Δ), respectively, were obtained from the corresponding cloned genomes, were gel-purified and recirculated in the presence of T4 DNA ligase (BioLab) overnight at 16° C. before being transfected. Cells were additionally treated with 300 mM D-glucosamine at 24 h after transfection as described previously (49). For the infection test, the genome-transfected cells were subjected to three successive freeze-thaw cycles. The total lysates were collected and used to infect PCV-free PK15 cells. They were then subjected to glucosamine treatment as described above and analyzed by IFA after infection.

In vitro expressions of the GFP-ORF1, —ORF2 and —ORF3 constructs were tested in transient expression experiments using PK15 cells. The cells grown in 25×25 mm flasks were transfected with GFP vector only, GFP-ORF1, GFP-ORF2, or GFP-ORF3 (2 µg of plasmid per flask), using LipofectaminePlus (GIBCO/BRL, USA), as described in the manufacturer's protocol. After 24 h posttransfection, the expression of ORF1, ORF2 and ORF3 was demonstrated by immunoblotting analysis using mouse anti-ORF1, ORF2 (Liu and Kwang, personal data), or ORF3 polyclonal antibodies.

RT-PCR

Total cell RNA was prepared from virus-infected PK15 cells by using Trizol RNA Extract reagent (Invitrogen) for reverse transcription-polymerase chain reaction (RT-PCR) of the ORF3 gene. The RNA samples were incubated with DNase I for 60 min at 37° C. to remove any contaminating viral DNA. The sense primer and the antisense primers were R671: 5'-ATGGTAACCATCCCACCACTTG-3' and F357: 5'-TTACTGATAGAATGTGGAGC-3', respectively. The suffix (F or R) of the oligonucleotide indicates the orientation of the primer. F indicates forward direction from nt 0 to 1767, while R indicates reverse direction from nt 1767 to 0. RT-PCR was carried out by using AMV Reverse Transcriptase kit (Roche) and Expand High Fidelity PCR kit (Roche) and the PCR product was electrophoresed in 1.2% agarose gel and photographed.

In Situ Hybridization (ISH)

ISH was carried out as described below. Briefly, PK15 cells grown in chamber slides (IWAKI) until 80% confluence were infected with the wild-type PCV2 or mutant PCV2 at a MOI of 1 $TCID_{50}$ (50% tissue culture-infective doses). The slides at 24, 48, 72, and 96 h postinfection were washed with PBS, fixed in 4% paraformaldehyde solution in PBS for 30 min at room temperature (RT), and dried. After acetylation in 0.1 M triethanolamine, 0.2 N HCl, and 0.5% acetic anhydride, the slides were prehybridized in hybridization solution (50% formamide; 5×SSC; 50 μg of salmon sperm DNA/ml) for 2 h at 60° C., followed by overnight hybridization at 60° C. with the digoxigenin (DIG)-labelled RNA probes at a concentration of 1 μg/ml. After being washed, the slides were incubated with anti-fluorescence-AP (Roche) (150 μl of 1:5,000 diluted in buffer [10% fetal calf serum; 100 mM Tris-HCl; 150 mM NaCl, pH 7.5]) overnight at 4° C. The slides were washed, incubated with NBT-BCIP mixture, and mounted for examination under the microscopy.

The sense riboprobe was synthesized by in vitro transcription with T7 RNA polymerase from pSK plasmid containing the cDNA of ORF3, which was linearized with KpnI. For the antisense riboprobe, an ORF3 fragment was amplified using a pair of primers (forward primer: 5'-ATGGTAACCATC-CCACCATTGTTTCTAGGTGGTTTCCAG-3', reverse primer: 5'-TAATACGACTCACTATAGGTCA-GAAATTTCCGCGGGCTGG-3', T7 promoter was underlined) and transcribed with T7 RNA polymerase. Both RNA probes were labelled using NTP-DIG label mix (Roche).

Assay for Replication of PCV2

To analyze the growth characteristics of PCV2, confluent PK15 cells were infected with the wild type, recombinant, or mutant PCV2 virus stock (generated after three passages in PK15 cells) at a MOI of 1 $TCID_{50}$. Infected cell cultures were harvested from the cells at different time intervals by three cycles of freeze-thawing followed by clarification. The titer of infectious virus present in the cell culture was determined by IFA on PK15 cells as described previously (14).

Apoptosis Assay

PK15 cells grown on chamber slides (IWAKI) at 24, 48, 72 and 96 h postinfection were fixed with 4% paraformaldehyde (PFA) in PBS and stained with porcine anti-PCV2 serum and FITC-conjugated antibody. For transfection, transfected PK15 or Cos-7 cells with GFP-ORF1, GFP-ORF2, or GFP-ORF3 plasmid were fixed with 4% PFA at 24 and 48 h posttransfection, respectively. The slides were then incubated with DAPI (2,4-diamidino-2-phenylindole) at a concentration of 1 μg/ml for 30 min at 37° C. and examined under LSM 510 META confocal laser scanning microscopy (Zeiss, Germany) with a Plan-Novofluar 63×/1.4 oil objective.

Infected PK15 cells ($2-3\times10^6$) at different intervals postinfection were harvested and centrifuged at 1,000×g for 10 min at 4° C. Pellets were washed in PBS and fixed in 2.5% glutaraldehyde. Subsequently, the cells were post-fixed in 1% $S_2O_4$ and embedded in EPON-812. Ultrathin sections were cut and examined under Hitachi H-700 electron microscopy.

PK15 cells grown on 75×75 mm flasks were infected with the wild-type PCV2. Following treatment, floating and trypsin-detached cells were pooled and washed twice with ice-cold PBS and fixed in 70% cold ethanol, then washed twice in PBS. After centrifugation, the cell pellets were stained in PBS propidium iodide (50 μg/ml) and treated with RNase A (100 μg/ml) for 45 min. DNA content of PK15 cells was analyzed by fluorescent activated cell sorting (FACSort, Becton Dickinson). At least 10,000 events were analyzed, and the percentage of cell in the sub-G1 population was calculated. Aggregates of cell debris at the origin of the histogram were excluded from the analysis of sub-G1 cells. In each experiment, mock-infected PK15 cells were used as controls and compared with cells infected with PCV2.

Adherent and nonadherent cells from infected cells with the wild-type PCV2 or transfected cells with GFP-ORF1, GFP-ORF2, or GFP-ORF3 plasmid were collected separately, sedimented at 200×g for 10 min, washed with ice-cold PBS, fixed in 4% PFA, stained with 1 μg/ml DAPI, and examined by florescence microscopy. A minimum of 300 cells/sample was scored for apoptotic changes (fragmentation of the nucleus into multiple discrete fragments).

Indirect Fluorescence Assay (IFA)

For infection, PK15 cells grown on the chamber slides (IWAKI) were incubated with the wild type, recombinant, or mutant PCV2 for 60 min at 37° C. at a MOI of 1 $TCID_{50}$ and added to MEM for incubation. Following the incubation at 37° C., cells at 24, 48, 72 and 96 h post-infection were washed with PBS and fixed for 30 min at RT with 4% PFA in PBS. After fixation, the cells were blocked by PBS-T with 3% BSA at RT for 1 h. Primary antibody, mouse anti-ORF3 polyclonal antibodies, or porcine anti-PCV2 antibody, was diluted in PBS-T with 1% BSA and incubated with the cells for 1 h at 37° C. After washing with PBS, the cells were incubated with rabbit anti-mouse or anti-porcine FITC-conjugated antibody (Sigma) diluted in PBS-T with 1% BSA for 1 h at 37° C. The cells were washed three times with PBS, rinsed in $dH_2O$, dried and mounted with fluorescence mounting media, and examined using fluorescence microscopy.

Western Blot Analysis

The whole cell lysates from the wild-type PCV2-infected PK15 cells were resolved on 15% SDS-polyacrylamide gel electrophoresis (SDS-PAGE) and blotted onto nitrocellulose (NC) membranes (Stratagene) with a semidry transfer cell (Bio-Rad Trans-Blot SD). The membranes were blocked for 2 h at RT in blocking buffer TBST (20 mM Tris-HCl [pH 7.4], 150 mM NaCl, 0.1% Tween-20) containing 5% skim milk powder to prevent nonspecific binding, and then incubated with mouse anti-ORF3 antibody at RT for 2 h. Then, the membranes were washed three times with TBST, and incubated for 1 h at RT with horseradish peroxidase-conjugated anti-mouse secondary antibody (DAKO) diluted in blocking buffer (1:2,000). After washing, the membrane was reacted with 3,3'-diaminobenzidine tetrahydrochloride (Pierce, Rockford, Ill., USA) substrate (20 ml 0.1 M pH 7.4 Tris-HCl, 20 mg DAB, and 6.8 μl $H_2O_2$), and then the reaction was stopped with distilled water.

Immunization and Live Vaccine Dosage

In the present study, TCID50 attenuated mutant PCV2 cells were administered to each group of experimental Balb/c white mice via both internasal and interperitoneal routes.

Pathological and Immunohistochemistry Studies

Necropsy of selected organs was performed on all the animals. Samples of the lung, liver and lymph nodes were collected and fixed by immersion in 4% DEPC-treated phosphate buffered paraformaldehyde. Fixed samples were dehydrated, embedded in paraffin wax, and sectioned at 6 μm, then stained with haematoxylin and eosin (HE). All samples were assessed for any signs of physical deterioration or microscopic lesions. The lymphoid organs were also assessed for depletion of lymphoid cells, infiltration by histocytic cells and/or the presence of multinucleated cells.

The avidin-biotin-peroxidase technique was used for the immunohistochemistry study. Tissues sectioned at 5 μm were placed on silane-coated slides. Endogenous peroxidase activity was inhibited by flooding the slides with 3% $H_2O_2$ in phosphate buffered saline with 1% Triton for 10 min. Blocking was carried out using 5% normal mouse serum for 1 h at room temperature. The sections were then incubated overnight at room temperature with purified PCV2 primary antibody raised in swine, diluted 1 in 100 in PBS-Triton. Biotinylated anti-swine and peroxidase-conjugated avidin was applied to the slides for 1 h at room temperature at a dilution of 1 in 200. The sections were then incubated in diaminobenzidine (DAB)-hydrogen peroxide solution for 5 min, and counterstained with 1% Methyl Green, dehydrated and mounted with Permount (Fisher Scientific Inc.) and examined microscopically.

Example 1

Identification of a Novel Viral Protein ORF3 in PCV2-Infected Cells

Figure 1C:
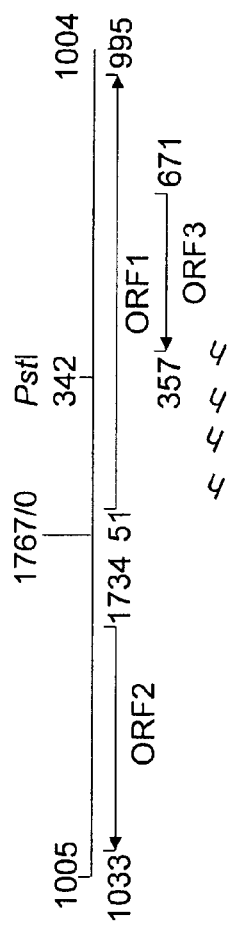
Figure 1D:
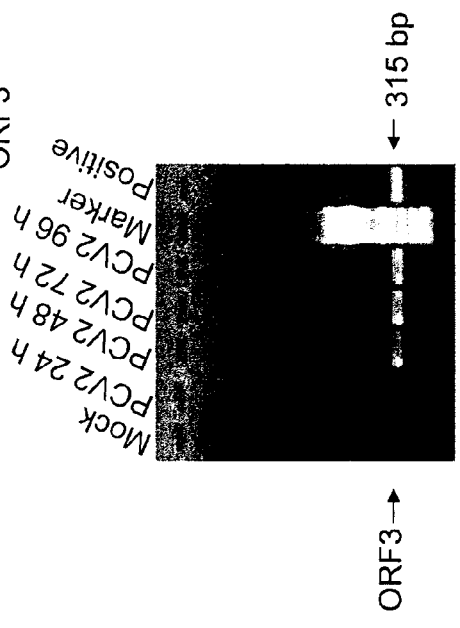
Figure 1E:
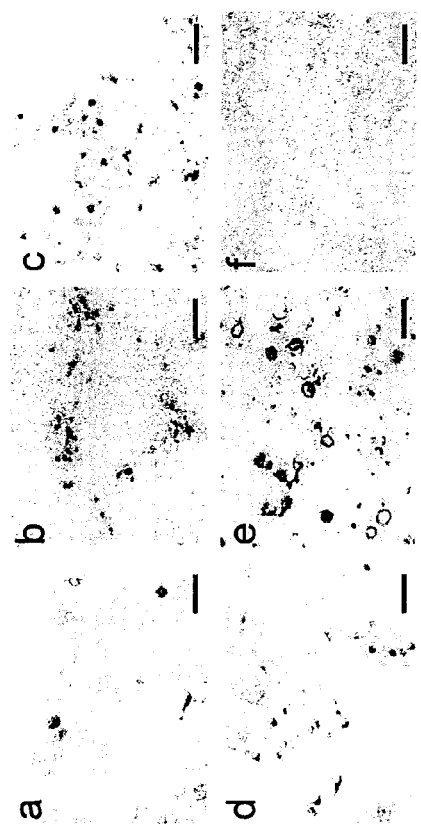

The whole-cell nucleic acid of infected and mock-infected PK15 cells was analyzed by reverse transcription (RT)-PCR. Amplified products were separated by agarose gel electrophoresis (FIG. 1D). A 315-bp fragment, ORF3 gene, was amplified using RNA isolated from PCV2-infected cells at the time indicated, suggesting that the ORF3 gene can be expressed at the transcription level in the PCV2-infected cells. PCV2 infected PK15 cells were further analyzed to determine the relative distribution of the ORF3 mRNA. As shown in FIG. 1E (panels a-d), the signals of ORF3 mRNA were detected in PCV2 infected cells at the time indicated using the antisense riboprobe, and was observed to be located predominantly in the nucleus of the infected cells. Interestingly, the mRNA signals were also detected in the infected cells (FIG. 1E, panel e) by using the sense ORF3 riboprobe. This could be explained as the full ORF3 gene is completely overlapping the ORF1 gene at the counter-direction in the PCV2 whole genome (FIG. 1C) and therefore ORF1 mRNA signals were detected. In addition, no signals were detected in control cells without PCV2 infection (FIG. 1E, panel f). The results further indicated that the ORF3 mRNA could be detected in PCV2-infected cells and is located in the nucleus.

The ORF3 gene was cloned into E. coli vector PQE30 and expressed (data not shown). This recombinant protein was further confirmed by the Western blotting using anti-histidine monoclonal antibody (data not shown) and could be prepared for production of monospecific antibody against the protein ORF3 which was used in the following experiments.

Figure 2A:
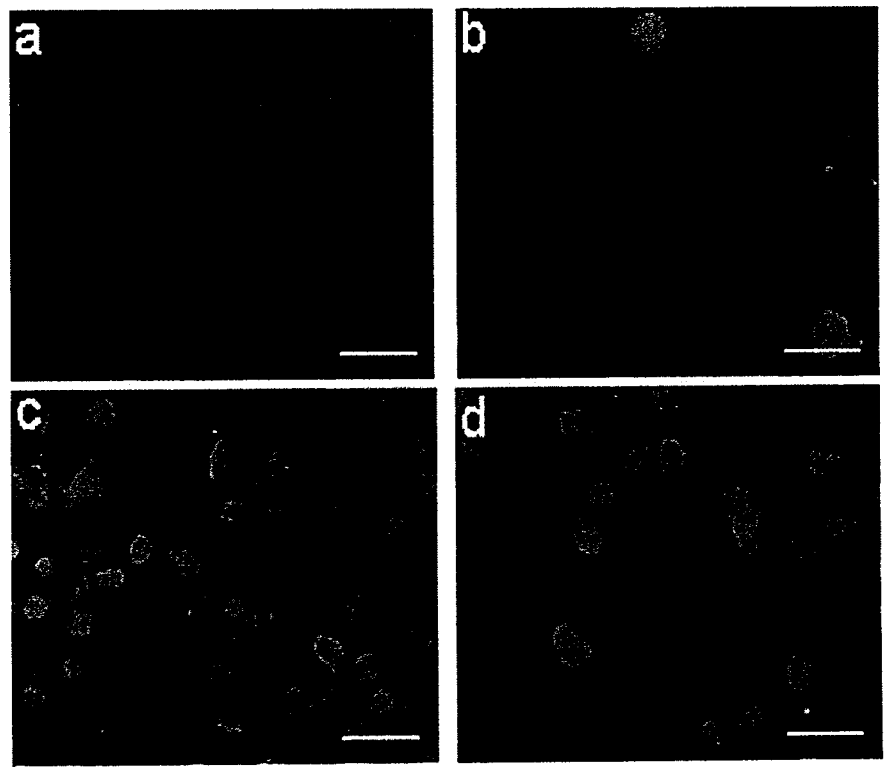
FIG. 2 Expression of ORF3 protein in PCV2-infected cells. (A) PCV2-infected PK15 cells were probed with antiserum raised against the ORF3 protein of PCV2. IFA staining of PK15 cells after infection with the PCV2 strain BJW at 24 (b), 48 (c), and 72 (d) h of postinfection. (a) was used as a negative control when mock-infected PK15 cells were stained by IFA. The cells were visualized and photographed using fluorescence microscopy. ORF3 antigen was located in the nucleus and to a lesser degree in the cytoplasm of the infected cells. Bars, 10 μm. (B) Total cell lysates from the PCV2 strain BJW-infected PK15 cells were electrophoresed in a 15% SDS-PAGE, transferred to nitrocellulose membrane, and detected by antiserum against ORF3 antibody. ORF3 protein was expressed in the PCV2-infected cells after infection.
Figure 2B:
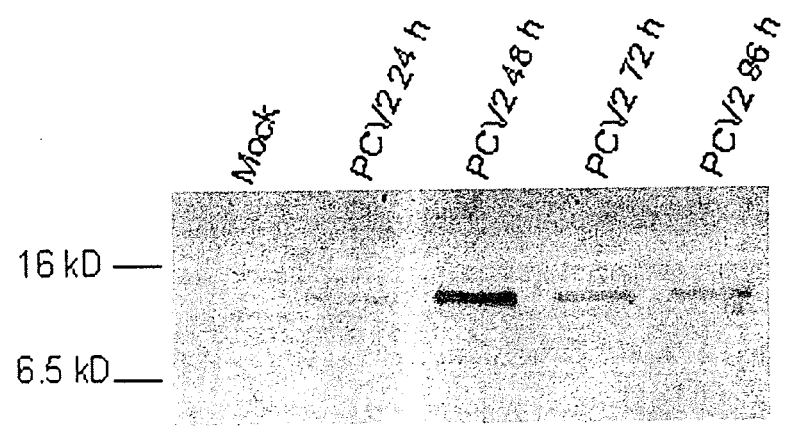

To determine whether ORF3 protein was expressed in PCV2-infected PK15 cells, cells were infected with PCV2 (strain BJW) as described in Materials and Methods. Anti-ORF3 mouse polyclonal antibody was used in direct immunofluorescence experiments to determine the expression and localization of ORF3 in PCV2-infected PK15 cells. Clusters of cells expressing ORF3 can be detected in cells that have been infected with PCV2 at 24, 48, 72, and 96 h (FIG. 2A, panels b-d, and data not shown) postinfection. The ORF3 protein was predominantly located in the nucleus and to a lesser degree in the cytoplasm of the infected cells. As shown in FIG. 2A (panel c), the ORF3 protein was maximally expressed in the infected cells at 48 h of postinfection. No significant staining was observed in mock-infected cells (FIG. 2A, panel a), indicating the specificity of the mouse antibody against ORF3. Total proteins were further harvested from PK15 cells at the times indicated postinfection and subjected to Western blotting (FIG. 2B). By using the mouse anti-ORF3 antibody, the protein was detected in PCV2-infected cells at 24 h postinfection as a faint, but clearly discernible signal. The intensity of the bands increased considerably thereafter but decreased at 72 h postinfection. No signal was detected in mock-infected cells (FIG. 2B). Together, these results show that the ORF3 is considered as a novel viral protein due to its expression at both transcription and translation levels in PCV2-infected cells.

Two major open reading frames have been identified within the genome of PCV. The cap gene ORF2, encodes viral capsid, the major structural protein. The other gene, rep gene (ORF1), directs the synthesis of the two Rep isoforms, Rep and Rep', which are essential for viral replication (9, 25). In addition, six more RNAs (three Rep-associated RNAs Rep3a, Rep3b and Rep3c, and three NS-associated RNAs NS515, NS672 and NS0) of PCV2 were detected during productive infection in porcine kidney cells (9, 10), suggesting that these transcription units did not have any effect on viral protein synthesis or DNA replication. NS515, NS672, and NS0 have been considered to be transcribed from three different promoters inside ORF1 downstream of the Rep promoter (9), and might not code for any proteins or functional proteins. Among the nine PCV2-specific RNAs identified, only ORF2 RNA is transcribed from the complementary DNA strand and encodes the viral capsid protein ORF2. In this present study, we have detected a novel viral RNA transcribed from the complementary DNA strand of the genome in PCV2-infected PK15 cells and further demonstrated that it encodes a novel viral protein (termed ORF3 here), which is involved in PCV2-induced apoptosis in cultured cells.

This novel transcript ORF3 RNA was readily detected by RT-PCR in PCV2-infected cells (FIG. 1D) and further detected in the nucleus of the infected cells by using ISH assay (FIG. 1E). Furthermore, using specific antibody against the ORF3 antigen, we have shown by immunofluorescence that the protein is expressed in PK15 cells infected with PCV2 (FIG. 2A) and predominantly located in the nuclei of the infected cells and to a lesser degree in the cytoplasm (FIG. 2A). The protein expression in the infected cells could also be detected by Western blot analysis (FIG. 2B). Analysis of the sequences of over 20 different geographic PCV2 isolates (obtained from GenBank database) suggested that the ORF3 protein is highly conserved in PCV2 strains studied, with greater than 94.5% identity at the amino acid level (data not shown). However, the corresponding region of PCV1 strains appears to be different and shows only 61.5% amino acid sequence identity. Since PCV1 viruses are naturally non-pathogenic and do not cause any pathological lesions in pigs (3, 48), these residues may play a role in the pathogenicity of the virus.

Example 2

ORF3 is not Essential for Viral Replication

As described, the ORF3 gene was deleted by point mutation of start codon ATG to GTG to generate PCV2 mutant lacking ORF3 gene (FIG. 1B). To study the function of the ORF3 protein in viral replication, PK15 cells were transfected with the wild-type PCV2 or mutant PCV2 infectious clone DNA. While the wild-type PCV2 DNA generated recombinant PCV2 (rPCV2) as expected, the PK15 cells transfected with the mutant PCV2 DNA also generated a viable mutant virus (rPCV2ORF3Δ). The mutant virus was passaged three times in PK15 cells to increase virus titers. Thereafter, the whole-cell nucleic acid of infected and mock-infected cells was analyzed by RT-PCR. Reaction products were separated by agarose gel electrophoresis (data not shown). A 315-bp fragment was amplified by using RNA isolated from the mutant PCV2-infected cells as seen in the wild-type PCV2-infected cells, indicating that point mutation occurring in the start codon of ORF3 gene did not affect its transcription and further suggests that the start site of ORF3 transcription may be located upstream. No PCR product was obtained using mock-infected PK15 cells. Sequence analysis of the RT-PCR products confirmed the presence of the desired alteration in the generated PCV2 mutant (data not shown). In addition, mRNA signals of ORF3 gene were detected in the nucleus of the mutant PCV2-infected cells by using the anti-sense ORF3 riboprobe (data not shown).

Figure 3:
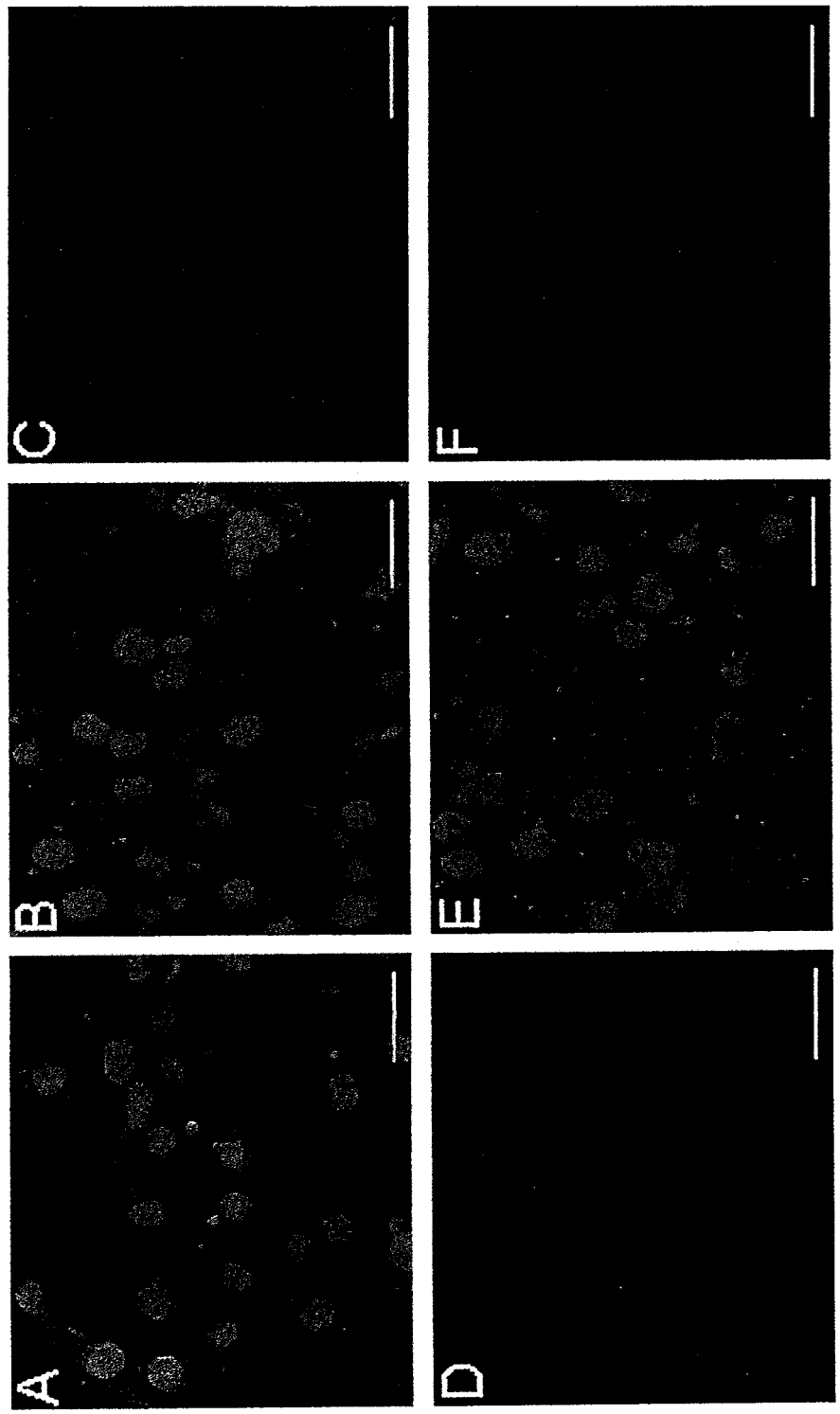
FIG. 3 IFA staining of ORF3-deficient PCV2-infected cells used to detect ORF3 protein expression. PK15 cells were infected with recombinant PCV2 virus stock (A and B) or with passage 5 of the ORF3-deficient PCV2 virus stock (D and E) at a MOI of 1. Mock-infected PK15 cells were used as negative controls (C and F). At 48 h postinfection, the cells were fixed and analyzed by immunofluorescence staining with mouse anti-ORF3 serum (A, D, and F) or porcine anti-PCV2 serum (B, C, and E). Bars, 10 μm.

To detect the expression of the ORF3 protein, PK15 cells were infected with the recovered viruses and analyzed by IFA using ORF3-specific antiserum. FIG. 3 shows the results of immunofluorescence staining of recombinant or mutant PCV2-infected cells. Cells infected with rPCV2 virus expressed ORF3 protein and gave a positive immunofluorescence signal (FIG. 3A). However, cells infected with mutant rPCV2ORF3Δ virus failed to give any fluorescenc signal (FIG. 3D), indicating the absence of ORF3 protein expression, even after passage 12 (data not shown). In contrast, anti-PCV2 porcine serum readily detected viral antigens in the nucleus of the recombinant as well as mutant PCV2 infected cells (FIGS. 3B and E). No fluorescence was detected in the mock-infected cells using anti-ORF3 mouse serum (FIG. 3C) or anti-PCV2 porcine serum (FIG. 3F).

To determine the replication kinetic of the wild-type, recombinant, and ORF3-deficient PCV2, PK15 cells were infected with each virus and the virus titer was determined by IFA assay at 5 days after infection. FIG. 4A depicts the growth curve of each virus (expressed as $TCID_{50}$/milliliter) at different times postinfection. The $TCID_{50}$ at the different time points after infection showed that the mutant virus (lacking the expression of ORF3 protein) replicated somewhat more slowly than the parent virus PCV2 or recovered recombinant PCV2 (rPCV2) virus. At 36 h after infection, the ORF3-deficient PCV2 virus showed a titer approximately 33- or 31-fold lower than that of the parent virus PCV2 or recovered rPCV2 virus, respectively. However, at 72 h postinfection, the ORF3-deficient PCV2 virus reached a titer of $10^{5.5}$ $TCID_{50}$/ml, which was similar to those of the parent virus PCV2 ($10^{5.8}$ $TCID_{50}$/ml) and recovered rPCV2 virus ($10^{5.6}$ $TCID_{50}$/ml). These results indicate that the ORF3 protein is not required for replication in cell culture.

Figure 4:
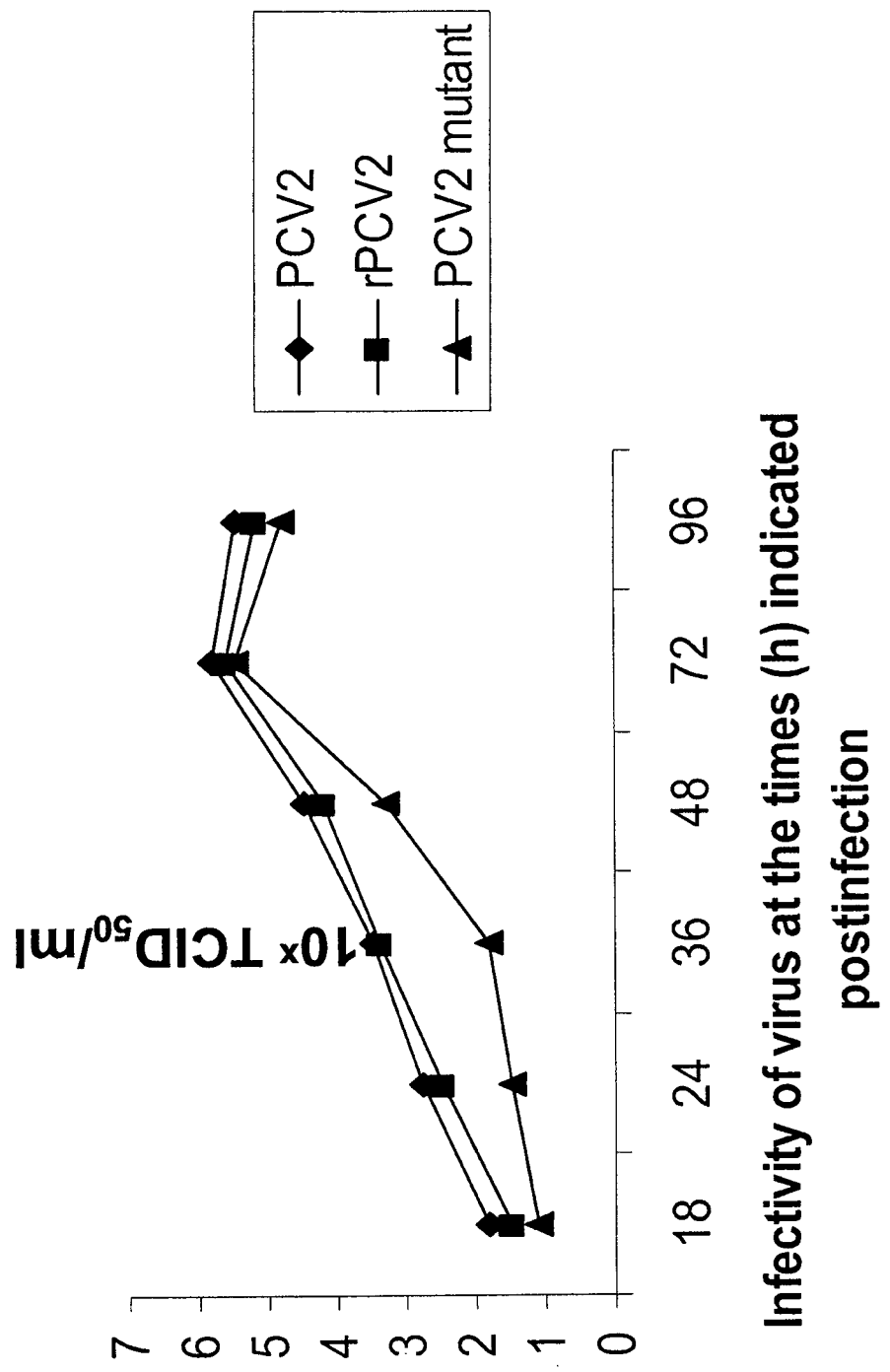
FIG. 4 Replication kinetics of ORF3-deficient PCV2 as well as recombinant PCV2 and wild-type PCV2. PK15 cells were infected with the indicated viruses at a MOI of 1 and harvested at the indicated time points, and infectious titers in $TCID_{50}$ per milliliter were determined by IFA.

In the absence of ORF3, in vitro replication of PCV2 is delayed (FIG. 4). However, the maximal titer is as high as those found after wild-type virus replication. It is conceivable that the delay in replication translates into attenuation in vivo, leading to a virus strain with vaccine potential. For PCV2, ORF2 protein has been considered as a major immunogenic capsid protein (9, 30, 31), and could stimulate protective response to pigs inoculated with baculovirus-expressed recombinant ORF2 (5) or injected with DNA vaccine from ORF2 (5, 19). Chimeric PCV1-2 virus with the ORF2 gene of PCV2 cloned into the nonpathogenic PCV1 genomic backbone could also induce a strong immune response against PCV2 while it is mildly pathogenic (5), suggesting that the ORF2 protein of PCV2 is a good host-protective immunogen. The immunodominant epitopes of the ORF2 protein have been further shown to likely locate within amino acid residues 47 to 84, 165 to 200, and the last four amino acids of the protein (22). These indicate that the antibody induced by the ORF3 protein might not be involved in the protective immune response to host. Also, the PCV2 mutant lacking the ORF3 protein could result in its failure to induce corresponding antibody in the animal and be expected to elicit an appropriate immune response as the wild-type PCV2.

Example 3

PCV2 Infection Induces Apoptosis in Cultured Cells

Figure 5A:
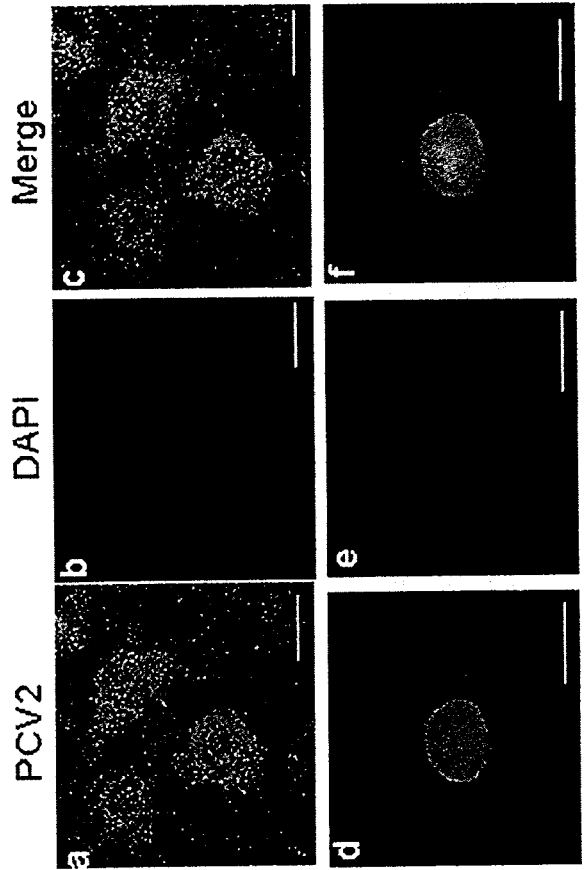
FIG. 5 PCV2 induces apoptosis in cultured PK15 cells. (A) PCV2-infected PK15 cells showed nucleosomal DNA fragmentation by DAPI staining. Cells infected with the PCV2 strain BJW at 48 (a and b) and 72 (d and e) h post-infection were detected by IFA using porcine serum against PCV2, and stained with DAPI, respectively. Overlaid images are shown in c and f. Bar, 10 μm. (B) Apoptosis induced by PCV2 was observed under an electron microscopy. Mock-infected cell (a), the complete nucleus (N) displayed a large, unique, electron-dense nucleolus (n). Cells at 48 (b) and 72 (c) h postinfection displayed typical markers of apoptosis such as chromatin condensed peripherally into a crescent-shaped mass (short arrow), and nuclear fragmentation, which forms apoptotic bodies, respectively. Bars, 2 μm.

PCV2 replication in PK15 cells during the late stage of infection resulted in cytopathic effects (CPE), such as rounding up, detachment of infected cells from the culture flask, and cell lysis and death. The mechanism that lead to the death of PCV2-infected cells are not fully understood. To determine whether PCV2 infection induced apoptosis in cultured cells, we inoculated PK15 cells with the wild-type PCV2 at a MOI of 1 $TCID_{50}$ and analyzed them for PCV2 viral antigen expression by IFA and apoptosis by DAPI staining at different times indicated postinfection. Intact nuclei are stained evenly, but apoptotic nuclei are often fragmented and show irregular or weak DNA staining caused by condensation and fragmentation of the DNA (45). FIG. 5A shows that chromatin condensation and fragmentation were visible in the PCV2-infected cells at 48 h (upper panel) and 72 h (lower panel) of postinfection. In contrast, no obvious nuclear morphological changes were observed in mock-infected cells after infection (data not shown).

Figure 5B:
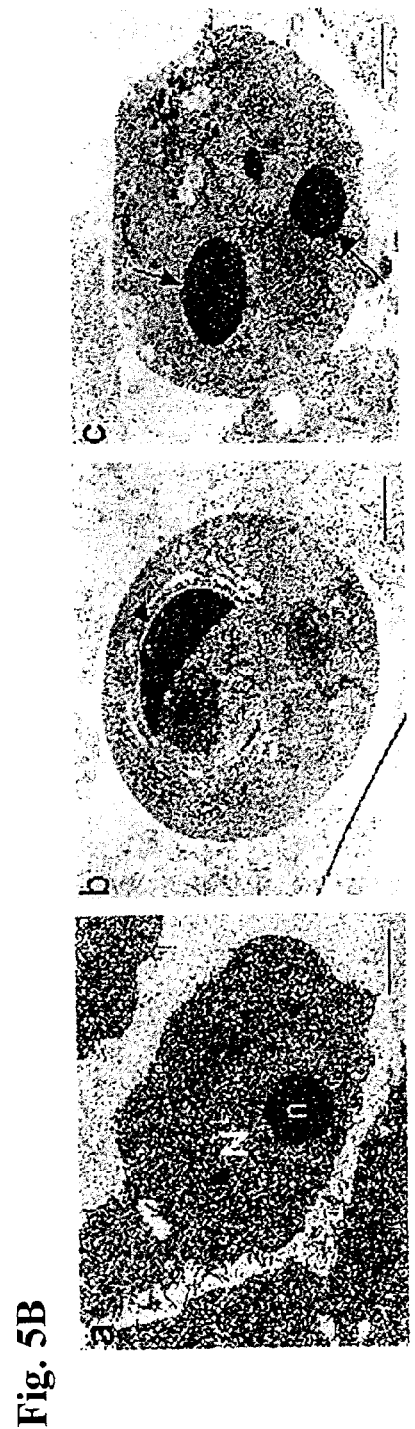

Infected and mock-infected PK15 cells were analyzed for their ultrastructural features. At 48 h postinfection, the cells infected with PCV2 showed features typical of programmed cell death, such as changes in the density and distribution of chromatin, which condensed peripherally into a crescent-shaped mass, and dilatation of nuclear cisternae were observed (FIG. 5B, panel b). At 72 h post-infection, cells displayed the typical markers of apoptotic cell death such as nuclear segmentation and cytoplasmic derangement, which are responsible for the formation of apoptotic bodies (FIG. 5B, panel c). At 96 h, cells exhibited further nuclear fragmentation, leading to extensive dispersion of apoptotic bodies (data not shown). In contrast, the mock-infected cells did not display detectable alterations at ultrastructural level (FIG. 5B, panel a).

The PCV2-induced apoptosis was assessed by determining the proportion of hypodiploid cells by flow cytometry of propidium iodide (PI)-stained, fixed PK15 cells. Apoptotic cells have a lower DNA content than normal cells and their presence is distinguished by the appearance of a hypodiploid peak of lower fluorescence. Under mock-infected cells, ~1% of cells were hypodiploid based on fluorescent activated cell sorting analysis of PI-stained cells (FIG. 6A). Whereas the hypodiploid cells increased significantly at 72 h postinfection subsequently decreased (FIG. 6A and data not shown). Induction of apoptosis by PCV2 was also scored by analysis of nuclear morphology by DAPI staining as described in Materials and Methods. Examination of stained cells demonstrated that apoptotic cells showed a similar manner (FIG. 6B) after infection as described in the flow cytometry analysis. As shown in FIG. 6C, more cells detached from the culture flask and entered into the substratum in the inoculate cultures than in the mock-inoculated cultures.

Virus-induced cell death plays an important role in the pathogenesis of virus infection. Apoptosis may represent an important step in the spread of progeny to neighboring cells while evading the host immune system (46), and function by eliminating aberrant cells created by DNA damage or those infected by viral pathogens (39). Many viruses have been demonstrated to elicit or inhibit apoptosis either directly or indirectly during their replication cycles (39). In the Circoviridae family, chicken anemia virus (CAV) induced apoptosis in thymocytes and cell lines after infection (18) and VP3 protein, apoptin encoded by CAV triggered apoptosis in various cultured transformed cell lines (34). For PCV2, it has been shown to induce apoptosis in B lymphocytes of affected swine followed by selective B lymphocyte depletion (43), and also trigger apoptosis in histiocytic cells in lymphoid tissues in a mouse model of PCV2 infection (21). But, contrary results have recently been reported that lymphocyte apoptosis is not significantly induced and caspase-3 activity not significantly stimulated in naturally affected pigs as compared to normal controls (24, 37), and suggested that lymphoid tissue depletion was mainly related to decreased proliferative activity in lymphoid tissue. However, we have demonstrated here that PCV2 was capable of inducing apoptosis in the cultured PK15 cells by using DAPI staining, electron microscopic observation, and flow cytometric analysis. The is DAPI staining showed irregular or weak DNA staining (FIG. 5A) caused by condensation and fragmentation of the DNA (45), which is consistent with the morphological changes under electron microscopic observation, including extensive chromatin condensation and appearance of apoptotic bodies (FIG. 5B). Apoptotic cells (FIG. 6B) determined by evaluation of the DAPI staining and hypodploid cells (FIG. 6A) analysed by flow cytometry increased significantly as compared to the mock-infected controls after PCV2-infection. 40% of the cells detached and floated into the substratum after infection with PCV2, whereas the floating cells in the mock-infected control were less than 5% (FIG. 6C). By expressing individual viral proteins in cultured cell line, we provided further evidence that a novel viral protein encoded by the ORF3 gene contribute to the induction of apoptosis during PCV2 infection.

Example 4

ORF3 Protein Alone Induces Apoptosis

Figure 7A:
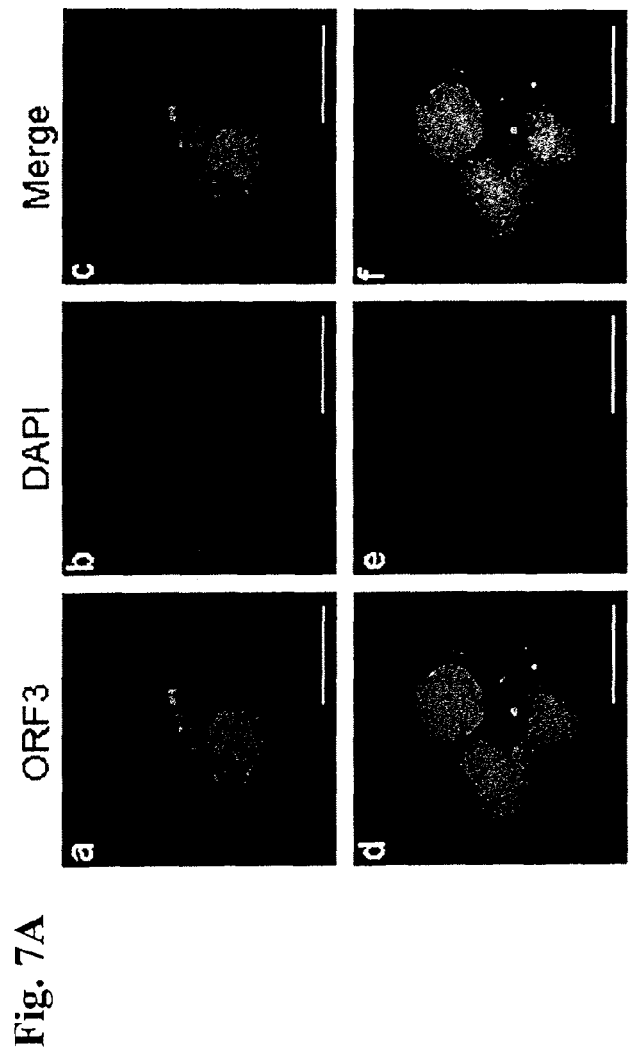
FIG. 7 ORF3 protein alone induces apoptosis in transfected cells. (A) PK15 and Cos-7 cells transfected with GFP-ORF3 plasmid at 24 h showed ORF3 expression (a and d) and nucleosomal DNA fragmentation (b and e) by DAPI staining, respectively. Overlaid images are shown in c and f. Bar, 10 mm. (B) Quantitative analysis of apoptosis induced by ORF3 protein. The average percentage of apoptotic cells of three experiments was scored by analysis of nuclear morphology by DAPI staining. (C) Shows the average percentage of detached cells of the three experiments as shown in B.
Figure 7B:
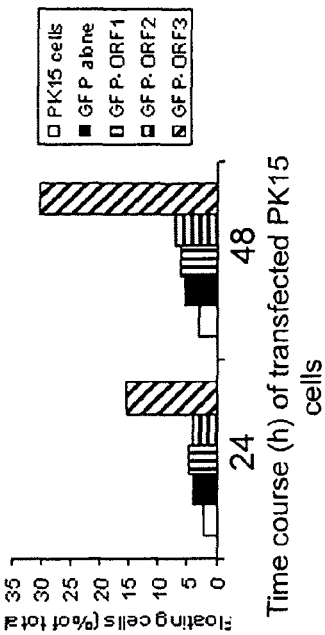
Figure 7C:
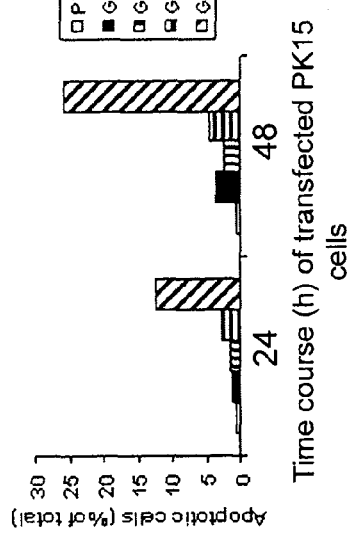

After confirming that PCV2 infection induces apoptosis in PK15 cells, the permissive cell line for PCV2 infection, we then tried to screen for PCV2-encoded proteins (virus-encoded proapoptotic proteins) that may be responsible for the induction of apoptosis. The ORF1, ORF2, and ORF3 genes were cloned into a mammalian expression vector pEGFP-C1 under the control of the human cytomegalovirus promoter. The PK15 and Cos-7 cells were transfected with these plasmids, and the expression of each protein was directly examined under the fluorescence microscopy and further confirmed by immunoblotting analysis using mouse anti-ORF1, ORF2, or ORF3 antibody (data not shown). The protein ORF1, ORF2, or ORF3 was localized to the transfected nucleus region similar to that seen in infected cells (data not shown). After transfection of cells with individual constructs, the cells were stained with DAPI at 24 and 48 h posttransfection. As shown in FIG. 7A, chromatin condensation and fragmentation, which are typical features of apoptosis, were seen in the ORF3-expressing PK15 cells (upper panel) and Cos-7 cells (lower panel) by nuclear DAPI-staining at 24 h posttransfection. In contrast, no obvious nuclear morphological changes were observed in ORF1 or ORF2-transfected cells (data not shown). Furthermore, the total GFP-positive cells and the number of cells with fragmented or condensed nuclei among the GFP-positive cells were counted, and the percentage of dead cells was calculated. As shown in FIG. 7B, expression of the ORF3 protein as GFP fusion constructs in transfected PK15 cells induced 10% and 25% of dead cells at 24 and 48 h posttransfection, respectively. The ORF3 protein also caused 12% and 28% of cell deaths at the time points when transfected into Cos-7 cells (data not shown). Expression of ORF1 and ORF2 proteins did not lead to more significant cell deaths than in the control in this screening, regardless of transfected PK15 (FIG. 7B) or Cos-7 cells (data not shown). In contrast, GFP alone could induce less than 4% of dead cells when transfected into both PK15 and Cos-7 cells at the time points of posttransfection (FIG. 7B and data not shown). Furthermore, more cells detached from the culture flask and entered the substratum in the ORF3-transfected PK15 (FIG. 7C) and Cos-7 cells (data not shown) than in the GFP alone transfection control as well as ORF1 or ORF2 transfected cells (FIG. 7C and data not shown).

To determine the apoptotic effects of rPCV2ORF3Δ in PK15 cells, the cells were infected with the mutant virus at a MOI of 1 TCID$_{50}$, harvested at different time intervals, and analyzed by caspase-3 activity. Apoptotic activity induced by the mutant virus was significantly lower than that produced by the wild-type PCV2 virus after infection (FIG. 9C). No appreciable level of apoptosis was detected in the mock-infected cells (FIG. 9C). The result indicates that PCV2-induced cell death is significantly reduced due to the absence of the ORF3 protein expression.

Infection of pigs with PCV2 results in lymphocyte depletion of follicular and interfollicular areas together with macrophage infiltration of lymphoid tissues followed by immunosuppression (42). ORF2 has been considered as a major capsid protein of PCV2, and could form virus-like particles after expression by baculovirus-expressed system (31), inferring that other viral proteins of PCV2 might be nonstructural proteins which are not necessary for virion assembly. Moreover, the ORF2 protein has been shown to express at a high level in the late stage of infection when PCV2 was inoculated to VIDO R1 cells (23). As also demonstrated by us, the ORF2 protein expression peaked at 72-96 h postinfection in PCV2-infected PK15 cells (data not shown). In this study, the ORF3 has been shown to have higher expression at both transcription and translation levels at 48 h in the PCV2-infected cells after infection (FIGS. 1 and 2), suggesting that the ORF3 might also be a nonstructural protein of PCV2. The nonstructural proteins of animal viruses might play an important role in viral replication and/or pathogenesis. For immunosuppressive virus, nonstructural protein VP3 of CAV was shown to cause apoptosis in lymphoblastoid T cells and was implicated in pathogenesis (34); nonstuctural protein VP5 of chicken infectious bursal disease virus, is not essential for viral replication (29) but is found to be involved in viral pathogenesis by its apoptotic activity (53). In our studies, we showed that the ORF3 protein of PCV2 is not required for viral replication in vitro and that PCV2-induced apoptotic activity was significantly reduced due to the absence of the ORF3 protein expression. Our data also suggest that the expression of ORF3 protein alone could induce apoptosis in transfected cells by activating the initiator caspase-8 followed by activation of the effector caspase-3 pathway similar to that in PCV2-infected cells. Together, the ORF3 protein might play a role in viral pathogenesis by its apoptotic activity. Induction of apoptosis of immune system cells might be one of requirements for virus-induced immunosuppression (12), this might facilitate the use of the ORF3-deleted mutant as a potential live vaccine strain against PCV2 infection. However, whether the use of such ORF3 protein-deficient virus can cause immunosuppression in pigs remains to be further determined.

Example 5

Pathological and Immunohistochemistry Studies

In this experimental set, one group of 8 weeks old balb/C mice was infected with ORF3-deficient PCV2 mutant (mPCV2), while another group was infected with the wild type PCV2. Normal healthy mice were used as negative control in this experiment. A post mortem examination of the mice 7, and 14 days postinfection was performed. Samples of the lymph nodes were fixed in 4% phosphate buffered paraformaldehyde. The tissues were dehydrated and stained with haematoxylin and eosin (HE) for histopathological examination. Serial sections were then stained by immunohistochemistry technique for PCV2 protein expression.

Figure 8A:
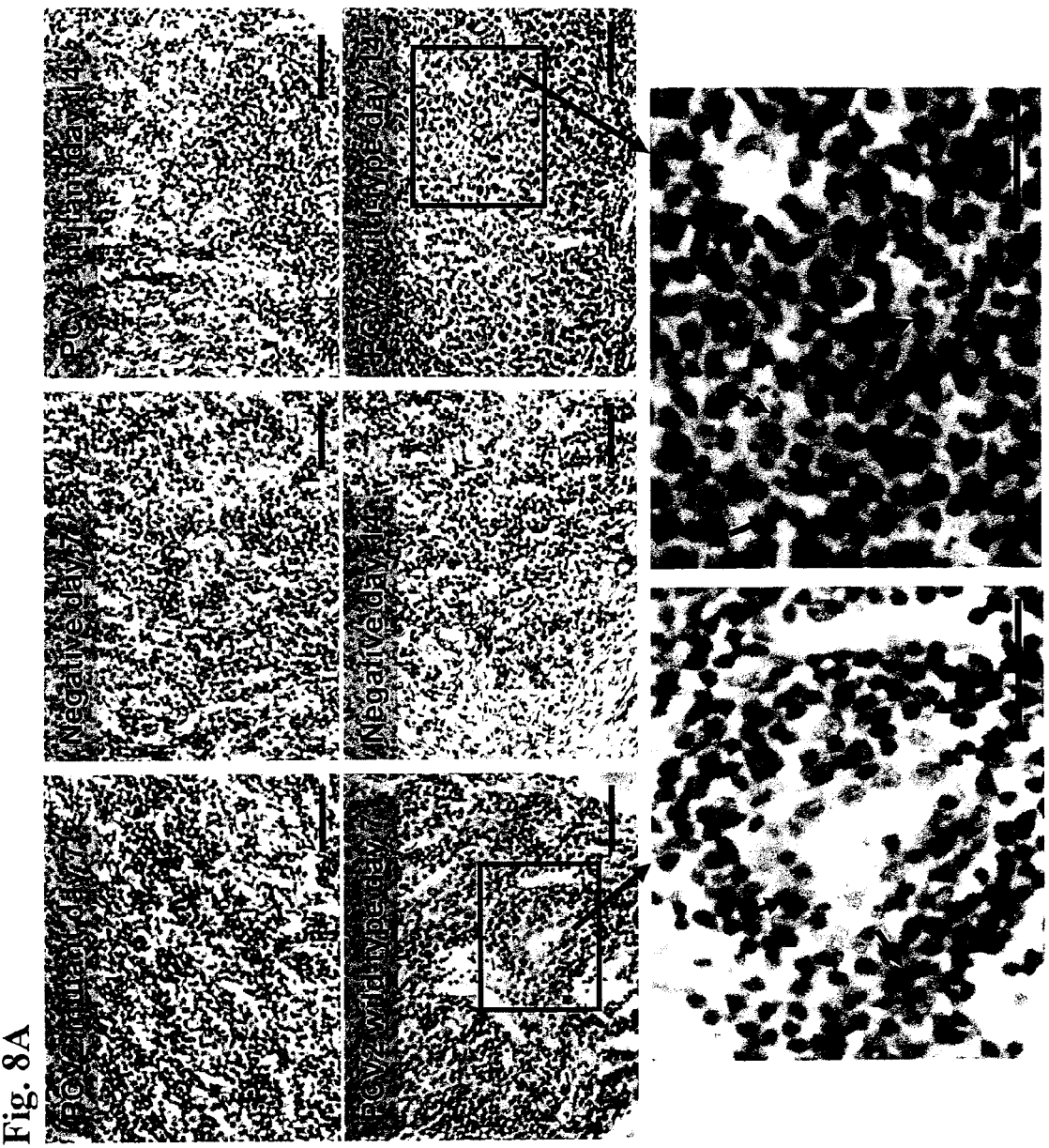
FIG. 8 (A) Histopathological examination of the inguinal lymph node of the three experimental groups showing the healthy and densely populated lymphocytes at the germinal centre of the negative control and mPCV2 group at days 7 and 14 postinfection. While the wild type PCV2 showing signs of histiocytic inflammatory infiltration with depletion of lymphoid cells at day 7 postinfection, and significant large numbers of apoptotic cells at day 14 postinfection (arrow). HE, Bar=200 μm (B) Inguinal lymph node of negative control showed the absence of PCV2 antigen, while the mutant PCV2 and wild type PVC2 at day 14 postinfection showed abundant presence of PCV2 antigen (stained dark brown) within the cytoplasm of the lymphocytes. In immunohistochemistry technique, Methyl Green counterstain, Bar=200 μm.

All negative control mice and mutant PCV2 infected mice on days 7 and 14 days postinfection showed no or slight physical signs of deterioration, however, the inguinal lymph node were slightly enlarged on day 14 postinfection. For wild type PCV2 infected mice, slight discoloration in the liver and slight enlargement of the inguinal lymph node were observed on day 7 postinfection. Significant discoloration of the liver and non-collapsed lung, and a significant enlargement of the mensenteric and inguinal lymph nodes were also observed in most of the wild type infected mice on day 14 postinfection. In FIG. 8A, histopathological examination of the inguinal lymph node of the three experimental groups showed healthy and densely populated lymphocytes at the germinal centre of the negative control and mPCV2 group, 7 and 14 days postinfection. While the wild type PCV2 showed signs of slight lymphocytes depletion at 7 days postinfection, varying degrees of lymphocytes depletion and significantly large numbers of apoptotic cells were also observed in different wild type PCV2 infected mice at 14 days postinfection (arrow).

Figure 8B:
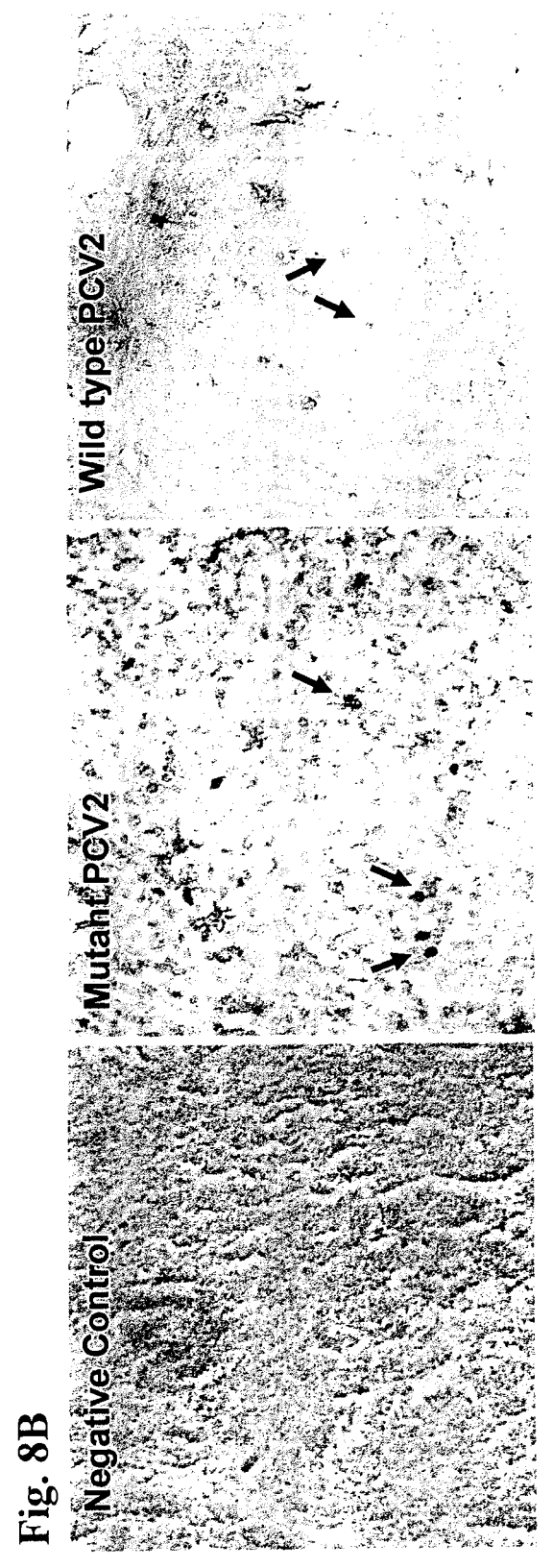

PCV2 antigen was detected in both the mutant PCV2 infected mice and the wild type infected mice. In all the tissues examined, immunolabelling of the PCV2 antigen were seen most abundantly within the cytoplasm of the lymphocytes and macrophages. However, the immunolabelling were significantly less intense in the wild type PCV2 infected mice at 14 days postinfection as compared to that of the mutant PCV2 infected mice. (as shown in FIG. 8B)

The lack of microscopic lesions and physical deterioration, in addition to the low levels of lymphocytes depletion and accumulation of high levels of the PCV2 antigen showed the protective efficacy and the replication ability of the mutant PCV2 strain. This evidence also reveals the potential of this mutant to become a suitable candidate for the production of an effective vaccine against PCV2 induced PMWS.

Our attenuated live vaccine mPCV2 is able to induce both the humoral and cellular responses in experimental mice. Not only is the virulence reduced but there is also no effect on its viral replication, thus providing continuous protective efficacy against PCV2 and will be a prime candidate for the vaccine conmercialisation.

Example 6

Generation of Apoptosis-Deficient PCV2 Mutants

The function of a point mutation in the ORF3 start codon in generating an apoptotic deficient virus has been discussed above. In this example, the inventors have identified functional mutable sites of the ORF3 other than the start codon mutation.

ORF3 is located within ORF1 at the opposite orientation. As ORF1 codes for replicase which is essential for virus replication, it is necessary to conserve the function of protein transcription of ORF1. Therefore redundant codons within ORF1 were selected for the generation of ORF3 mutants.

In order to create aberrant ORF3 expression, the inventors selected a strategy of changing the pattern of electrical charges in the amino acid sequence in order to affect the resulting secondary structure of the protein. For example, the inventors reversed the charge or made the charge neutral in particular amino acids at particular positions in the sequence. In this manner, protein function will be disabled. Site-directed mutagenesis method was employed in this study to introduce the above mentioned mutations into the viral genome.

Five mutants were designed and have been named according to the mutated amino acid numbers. Mutant 27 changed alanine to a stop codon as shown in SEQ ID NO. 19. Consequently this mutant expresses a truncated 26 amino acids ORF3 protein.

Other mutations changed the function of the ORF3 protein by altering the conformation of the protein as discussed above. In order to alter the conformation of the protein, charged amino acids in the protein were targeted for mutations. The alpha-helix region of the ORF3 protein is appropriate due to the presence of many charged amino acids. In mutants 52 and 61, the amino acid charges were reversed thereby altering the secondary structure of the protein in that the alpha region of the protein became unfolded. In mutant 52 the amino acid His+ was changed to Asp− by effecting the nucleotide sequence change as shown in SEQ ID NO. 20. In the mutant 61, the amino acid Glu− was changed to Lys+ by effecting the nucleotide sequence change as shown in SEQ ID NO. 21. In mutant 85, a positive charge was modified to a neutral charge as a result of changing His+ to Tyr by effecting the nucleotide sequence change as shown in SEQ ID NO. 22. As a result, the secondary structure of mutant 85 was changed in that one of the coil regions of the protein was opened.

Figure 10:
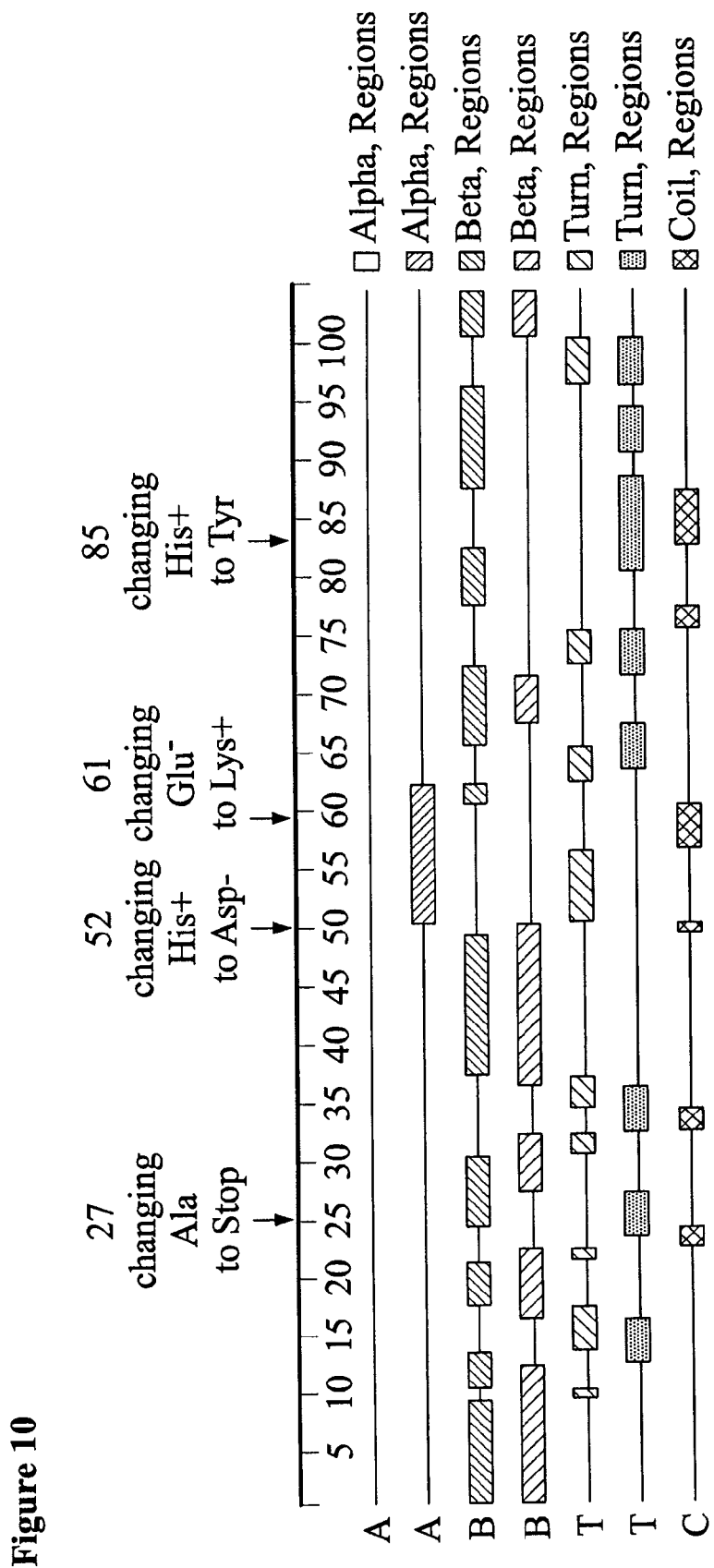
FIG. 10 Position of Mutations in ORF3. Mutant 27 changed Ala to a stop codon resulting in the expression of a truncated 26 amino-acid ORF3 protein. Mutants 52 and 61 reversed the amino acid charges by changing His+ to Asp− and Glu− to Lys+ respectively. Mutant 85 lost a positive charge by changing His+ to Tyr. The mutated viral genomes were transfected into the PK15 cells and let grew for 5 days. After 5 days, the cells were harvested and lysed by 3× freeze-thawing. Whole cell lysates were then used for infections of fresh PK15 cells.

Mutant Deletion 50-62 acts a control in which amino acid 50 to amino acid 62 were deleted. As described above, the mutants generated will not affect the amino acid sequence of ORF1 and therefore will have no effect on the transcription of replicase, as the mutation sites are at the redundant codons of ORF1. See FIG. 10.

Figure 11:
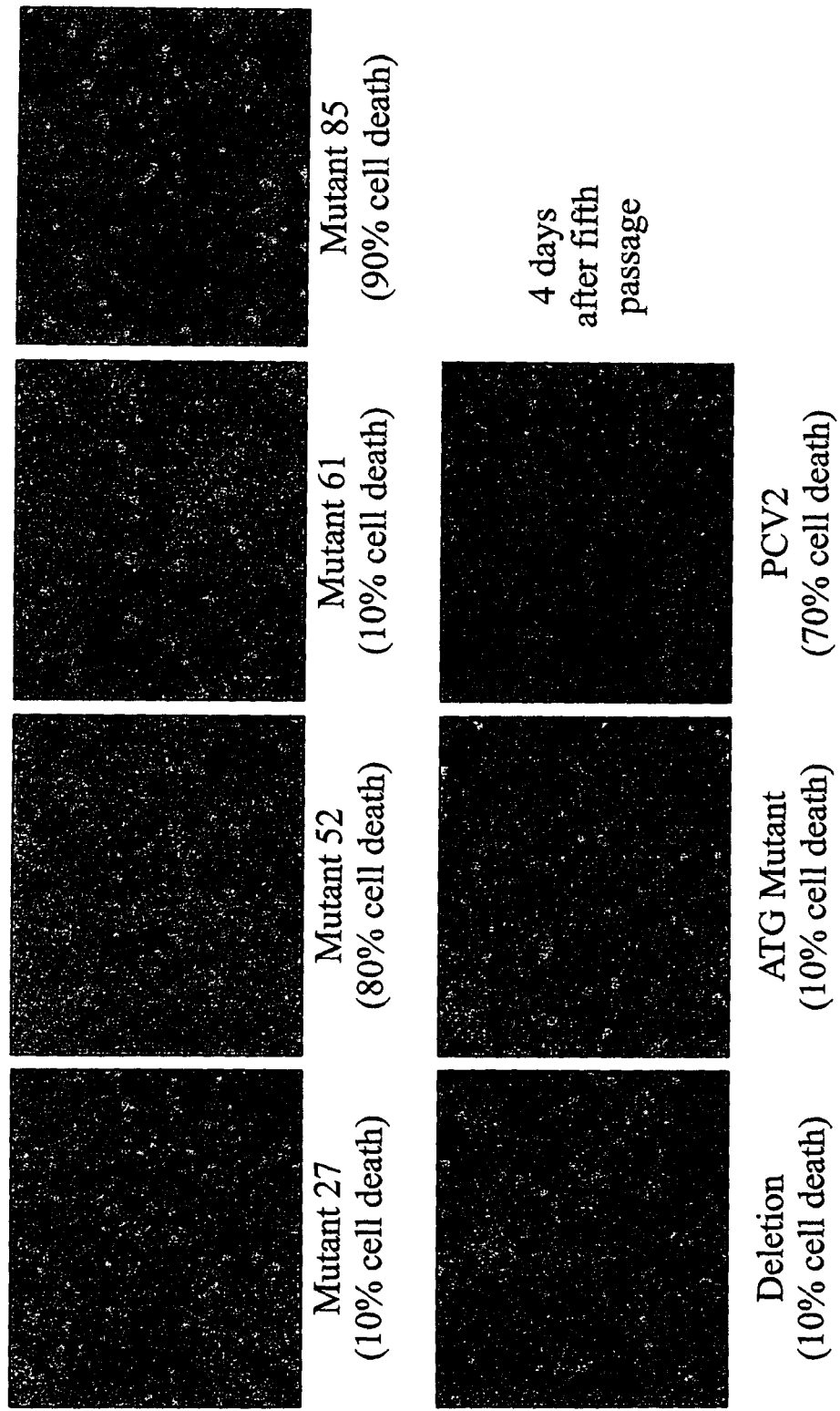
FIG. 11 Cell Death caused by apoptosis of cells transfected with mutants and PCV2 at four days after the fifth passage of cell culturing. Mutants 27, 61 and a mutant caused by deletion and mutation of the ATG start codon of ORF3 caused 10% cell death in contrast to 70-90% cell death for mutants 52, 85 and PCV2.

The mutated viral genomes were transfected into the PK15 cells and allow to grow for 5 days. After 5 days, the cells were harvested and lysed by 3× freeze-thawing. Whole cell lysates were then used for infections of fresh PK15 cells. At the fifth passage of cell culturing, mutants 52 and 85 as well as the wild type PCV2 started to exhibit cell death. About 70-90% cell death was observed in wild type PCV2, mutant 52 or mutant 85 infected PK15 cells. In contrast, mutant 61, mutant 27 or the mutant resulting from deletion mutation of ATG start codon of ORF3 all exhibited a significant reduction of cell death (about 10%). See FIG. 11.

Those mutants having low apoptosis rates are suitable for the production of a live-attenuated vaccine. Therefore the inventors have found that altering the conformation at particular amino acids at the nucleic acid level allows the production of mutants suitable for the production of live-attenuated viruses for vaccine production.

Furthermore it is possible to reduce the possibility of the virus reverting to the wild-type virulent form by combining such mutations into double or triple mutations. For example it is possible to combine the ATG mutation with the mutant 27 as shown in SEQ ID NO. 23 or the ATG mutation with the mutant 61 as shown in SEQ ID NO. 24. The above mutations can be combined into a triple mutation consisting of the ATG mutant, mutant 27 and mutant 61 as shown in SEQ ID NO. 25.

It will be apparent that various modifications and adaptations of the invention will be apparent to the person skilled in the art after reading the foregoing disclosure without departing from the spirit and scope of the invention and it is intended that all such modifications and adaptations come within the scope of the appended claims.

REFERENCES

1. Allan, G. M., and J. A. Ellis. 2000. Porcine circoviruses: a review. J. Vet. Diagn. Investig. 12:3-14.

2. Allan, G. M., S. Kennedy, F. McNeiry, J. C. Foster, J. A. Ellis, S. J. Krakowka, B. M. Meehan, and B. M. Adair. 1999. Experimental reproduction of sever wasting disease by co-infection of pigs with porcine circovirus and porcine parvovirus. J. Comp. Pathol. 121:1-11.
3. Allan, G. M., F. MeNeilly, J. P. Cassidy, G. A. Reilly, B. Adair, W. A. Ellis, and M. S. McNulty. 1995. Pathogenesis of porcine circovirus: experimental infections of colostrum deprived piglets and examination of pig foetal material. Vet. Microbiol. 44:49-64.
4. Ashkenazi, A., and V. M. Dixit. 1998. Death receptors: signalling and modulation. Science 281:1305-1308.
5. Blanchard, P., D. Mahe, R. Cariolet, A. Keranflec'h, M. A. Baudouard, P. Cordioli, E. Albina, and A. Jestin. 2003. Protection of swine against post-weaning multisystemic wasting syndrome (PMWS) by porcine circovirus type 2 (PCV2) proteins. Vaccine 21:4565-4575.
6. Bolin, S. R., W. C. Stoffregen, G. P. Nayar, and A. L. Hamel. 2001. Postweaning multisystemic wasting syndrome induced after experimental inoculation of cesarean-derived, colostrum-deprived piglets with type 2 porcine circovirus. J. Vet. Diagn. Invest. 13:185-194.
7. Budihardjo, I., H. Oliver, M. Lutter, and X. D. Wang. 1999. Biochemical pathways of caspase activation during apoptosis. Annu. Rev. Cell. Dev. Biol. 15:269-290.
8. Chae, C. 2004. Postweaning multisystemic wasting syndrome: a review of aetiology, diagnosis and pathology. Vet. J. 168:41-49.
9. Cheung, A. K. 2003. Transcriptional analysis of porcine circovirus type 2. Virology 305:168-180.
10. Cheung, A. K. 2003. Comparative analysis of the transcriptional patterns of pathogenic and nonpathogenic porcine circoviruses. Virology 310:41-49.
11. Cohen, G. M. 1997. Caspases: the executioners of apoptosis. Biochem. J. 326:1-16.
12. Drew, T. W. 2000. A review of evidence for immunosuppression due to porcine reproductive and respiratory syndrome virus. Vet. Res. 31:27-39.
13. Earshaw, W. C., L. M. Martins, and S. H. Kaufmann. 1999. Mammalian caspases: structure, activation, substrates, and functions during apoptosis. Ann. Rev. Biochem. 69:383-424.
14. Fenaux, M., P. G. Halbur, G. Haqshenas, R. Royer, P. Thomas, P. Nawagitgul, M. Gill, T. E. Toth, and X. J. Meng. 2002. Cloned genomic DNA of type 2 porcine circovirus in infectious when injected directly into the liver and lymph nodes of pigs: characterization of clinical disease, virus distribution, and pathologic lesions. J. Virol. 76:541-551.
15. Fenaux, M., T. Opriessnig, P. G. Halbur, and X. J. Meng. 2003. Immunogenicity and pathogenicity of chimeric infectious DNA clones of pathogenic porcine circovirus type (PCV2) and nonpathogenic PCV1 in weaning pigs. J. Virol. 77:11232-11243.
16. Green, D. R. 1998. Apoptotic pathways: the roads to ruin. Cell 94:695-698.
17. Janicke, R. U., M. L. Sprengart, M. R. Wati, and A. G. Porter. 1998. Caspase-3 is required for DNA fragmentation and morphological changes associated with apoptosis. J. Biol. Chem. 273:9357-9360.
18. Jeurissen S. H., F. Wagenaar, J. M. Pol, A. J. Van der Eb, and M. H. M. Noteborn. 1992. Chicken anemia virus causes apoptosis of thymocytes after in vivo infection and of cell lines after in vitro infection. J. Virol. 66:7383-7388.
19. Kamstrup, S., A. M. Barfoed, T. H. Frimann, A.-S. Ladekjær-Mikkelsen, and A. Bøtner. 2004. Immunisation against PCV2 structural protein by DNA vaccine of mice. Vaccine 22:1358-1361.
20. Kennedy, S., D. Moffett, F. McNemy, B. Meehan, J. Ellis, S. Krakowka, and G. M. Allan. 2000. Reproduction of lesions of postweaning multisystemic wasting syndrome by infection of conventional pigs with porcine circovirus type 2 alone or in combination with porcine parvovirus. J. Comp. Pathol. 122:9-24.
21. KIupel, M., G. W. Stevenson, J. Choi, K. S. Latimer, C. L. Kanitz, and S. K. Mittal. 2001. Viral replication and lesions in BALB/c mice experimentally inoculated with porcine circovirus isolated from a pig with postweaning multisystemic wasting disease. Vet. Pathol. 38:74-82.
22. Lekeharoensuk, P., I. Morozov, P. S. Paul, N. Thangthunmiyom, W. Wajjawalku, and X. J. Meng. 2004. Epitope mapping of the major capsid protein of type 2 porcine circovirus (PCV2) by using chimeric PCV1 and PCV2. J. Virol. 78:8135-8145.
23. Liu, Q. G., S. K. Tikoo, and L. A. Babiuk. 2001. Nuclear localization of the ORF2 protein encoded by porcine circovirus type 2. Virology 285:91-99.
24. Mandrioli, L., G. Sarli, S. Panarese, S. Baldoni, and P. S. Marcato. 2004. Apoptosis and proliferative activity in lymph node reaction in postweaning multisystemic wasting syndrome (PMWS). Vet. Immunol. Immunopathol. 97:25-37.
25. Mankertz, A., R. Caliskan, K. Hattermann, B. Hillenbrand, P. Kurzendoerfer, B. Mueller, C. Schmitt, T. Steinfeldt, and T. Finsterbusch. 2004. Molecular biology of porcine circovirus: analyses of gene expression and viral replication. Vet. Microbiol. 98:81-88.
26. Mankertz, A., J. Mankertz, K. Wolf, and H. J. Buhk. 1998. Identification of a protein essential for replication of porcine circovirus. J. Gen. Virol. 79:381-383.
27. Meehan, B. M., J. L. Creelan, M. S. McNulty, and D. Todd. 1997. Sequence of porcine circovirus DNA: Affinities with plant cicoviruses. J. Gen. Virol. 78:221-227.
28. Miyata, H., H. Tsunoda, A. Kazi, A. Yamada, M. A. Khan, J. Murakami, T. Kamahora, K. Shiraki, and S. Hino. 1999. Identification of a novel GC-rich 113-nucleotide region to complete the circular, single-stranded DNA genome of TT virus, the first human circovirus. J. Virol. 73:3582-3586.
29. Mundt, E., B. Köllner, and D. Kretzschmar. 1997. Vp5 of infectious bursal disease virus is not essential for viral replication in cell culture. J. Virol. 71:5647-5651.
30. Nawagitgul, P., P. A. Harms, I. Morozov, B. J. Thacker, S. D. Sorden, C. Lekcharoensuk, and P. S. Paul. 2002. Modified indirect porcine circovirus (PCV) type 2-based and recombinant capsid protein (ORF2)-based enzyme-linked immunosorbent assay for detection of antibodies to PCV. Clin. Diagn. Lab. Immunol. 9:33-40.
31. Nawagitgul, P., I. Morozov, S. R. Bolin, P. A. Harms, and S. D. Sorden. 2000. Open reading frame 2 of porcine circovirus type 2 encodes a major capsid protein. J. Gen. Virol. 81:2281-2287.
32. Nicholson, D. W., A. Ali, N. A. Thornberry, J. P. Vaillancourt, C. K. Ding, M. Gallant, Y. Gareau, P. R. Griffin, M. Labelle, Y. A. Lazebnik, N. A. Munday, S. M. Raju, M. E. Smulson, T.-T. Yamin, V. L. Yu, and D. K. Miner. 1995. Identification and inhibition of the ICE/CED-3 protease necessary for mammalian apoptosis. Nature 376:37-43.
33. Nishizawa, T., H. Okamoto, K. Konishi, H. Yoshizawa, Y. Miyakawa, and M. Mayumi. 1997. A novel DNA virus (TTV) associated with elevated transaminase levels in posttransfusion hepatitis of unknown etiology. Biochem. Biophys. Res. Commun. 241:92-97.
34. Noteborn, M. H. M., D. Todd, C. A. Verschueren, H. W. de Gauw, W. L. Curran, S. Veldkamp, A. J. Douglas, M. S.

McNulty, A. J. Van der Eb, and G. Koch. 1994. A single chicken anemia virus protein induces apoptosis. J. Virol. 68:346-351.
35. Phenix, K. V., J. H. Weston, I. Ypelaar, A. Lavazza, J. A. Smyth, D. Todd, G. E. Wilcox, and S. R. Raidal. 2001. Nucleotide sequence analysis of a novel circovirus of canaries and its relationship to other members of the genus Circovirus of the family Circoviridae. J. Gen. Virol. 82:2805-2809.
36. Pringle, C. R. 1999. Virus taxonomy at the XIth International Congress of Virology, Sydney, Australia. Arch. Virol. 144:2065-2070.
37. Resendes, A. R., N. Majó, J. Segales, E. Mateu, M. Calsamiglia, and M. Domingo. 2004. Apoptosis in lymphoid organs of pigs naturally infected by porcine circovirus type 2. J. Gen. Virol. 85:2837-2844.
38. Ritchie, B. W., F. D. Niagro, P. D. Lukert, W. L. Steffens III, and K. S. Latimer. 1989. Characterization of a new virus from cockatoos with psittacine beak and feather disease. Virology 171:83-88.
39. Roulston, A., R. C. Marcellus, and P. E. Branton. 1999. Virus and apoptosis. Annu. Rev. Microbiol. 53:577-628.
40. Salvesen, G. S., and V. M. Dixit. 1997. Caspases: intracellular signaling by proteolysis. Cell 91:443-446.
41. Schulze-Osthoff, K., D. Ferrari, M. Los, S. Wesselborg, and M. E. Peter. 1998. Apoptosis signalling by death receptors. Eur. J. Biochem. 254:439-459.
42. Segalés, J., M. Domingo, F. Chianini, N. Majó, J. Domínguez, L. Darwich, and E. Mateu. 2004. Immunosuppression in postweaning multisystemic wasting syndrome affected pigs. Vet. Microb. 98:151-158.
43. Shibahara, T., K. Sato, Y. Ishikawa, and K. Kadota. 2000. Porcine circovirus induces B lymphocyte depletion in pigs with wasting disease syndrome. J. Vet. Med. Sci. 62:1125-1131.
44. Takahashi, K., Y. Iwasa, M. Hijikata, and S. Mishiro. 2000. Identification of a new human DNA virus (TTV-like mini virus, TLMV) intermediately related to TT virus and chicken anemia virus. Arch. Virol. 145:979-993.
45. Telford, W. G., L. E. King, and P. J. Fraker. 1992. Comparative evaluation of several DNA binding dyes in the detection of apoptosis-associated chromatin degradation by flow cytometry. Cytometry 13:137-143.
46. Teodoro, J. G., and P. E. Branton. 1997. Regulation of apoptosis by viral gene products. J. Virol. 71:1739-1746.
47. Tischer, I., H. Gelderblom, W. Vettermann, and M. A. Koch. 1982. A very small porcine virus with circular single-stranded DNA. Nature 295:64-66.
48. Tischer, I., W. Mields, D. Wolff, M. Vagt, and W. Griem. 1986. Studies on epidemiology and pathogenicity of porcine circovirus. Arch. Virol. 91:271-276.
49. Tischer, I., D. Peters, R. Rasch, and S. Pociuli. 1987. Replication of porcine circovirus: induction by glucosamine and cell cycle dependence. Arch. Virol. 96:39-57.
50. Todd, D., F. D. Niagro, B. W. Ritchie, W. Curran, G. M. Allan., P. D. Lukert., K. S. Latimer, W. L. Steffens III, and M. S. McNulty. 1991. Comparison of three animal viruses with circular single-stranded DNA genomes. Arch. Virol. 117:129-135.
51. Todd, D., J. H. Weston, D. Soike, and J. A. Smyth. 2001. Genome sequence determinations and analyses of novel circoviruses from goose and pigeon. Virology 286:354-362.
52. Woods, L. W., K. S. Latimer, B. C. Barr, F. D. Niagro, R. P. Campagnoli, R. W. Nordhausen, and A. E. Castro. 1993. Circovirus-like infection in a pigeon. J. Vet. Diagn. Invest. 5:609-612.
53. Yao, K., and V. N. Vakharia. 2001. Induction of apoptosis in vitro by the 17-kDa nonstructural protein of infectious bursal disease virus: possible role in viral pathogenesis. Virology 285:50-58.

The invention claimed is:

1. An attenuated immunogenic porcine circovirus 2 (PCV2) virus, comprising a mutation in the start codon of ORF3 rendering the start codon non-functional, whereby the ORF3 protein is not expressed and the mutation in ORF3 of the virus does not result in a change in the sequence of amino acids of the protein encoded by ORF1.

2. A pharmaceutical composition, comprising:
an immunologically effective amount of a virus of claim 1; and
a pharmaceutically acceptable carrier, excipient, adjuvant or diluent.

3. An attenuated immunogenic porcine circovirus 2 (PCV2) virus, comprising a mutation in ORF3 that is one or both of an insertion of a stop codon as set forth in SEQ ID NO. 19, or a mutation of the alpha-helix region as set forth in SEQ ID NO. 21, wherein:
the mutated ORF3 protein has reduced ability to induce apoptosis compared to the wildtype ORF3 protein, whereby the virus is attenuated compared to the same virus that expresses a wildtype functional ORF3 protein; and
the mutation is a silent mutation with respect to the ORF1 protein so that the mutation does not result in any change in the sequence of amino acids of the protein encoded by ORF1.

4. The virus of claim 3, further comprising a mutation of the start codon.

5. A pharmaceutical composition, comprising:
an immunologically effective amount of a virus of claim 3; and
a pharmaceutically acceptable carrier, excipient, adjuvant or diluent.

6. An attenuated immunogenic porcine circovirus 2 (PCV2) virus, comprising a mutation in ORF3, wherein:
the virus is attenuated compared to the same virus that expresses a functional ORF3 protein;
the virus encodes a functional ORF1 protein;
the PCV2 virus comprises the capsid protein encoded by ORF2 to confer immunogenicity;
ORF3 protein is not expressed by virtue of a mutation of the start codon and a mutation in the alpha-helix region, whereby the ORF3 comprises the sequence of nucleotides set forth in SEQ ID NO. 23 or 24.

7. A pharmaceutical composition, comprising:
an immunologically effective amount of a virus of claim 6; and
a pharmaceutically acceptable carrier, excipient, adjuvant or diluent.

8. An attenuated immunogenic porcine circovirus 2 (PCV2) virus, comprising mutations in ORF3, wherein:
the virus is attenuated compared to the same virus that expresses a functional ORF3 protein;
the mutations in the ORF3 protein attenuate the virus compared to the PCV2 virus that expresses ORF3 protein of SEQ ID NO:1;
the virus encodes a functional ORF1 protein;
the virus comprises the capsid protein encoded by ORF2 to confer immunogenicity;
the ORF3 comprises the sequence of nucleotides set forth in SEQ ID NO. 25; and the mutations in ORF3 of the virus result in no change in the sequence of amino acids of the protein encoded by ORF1.

9. A pharmaceutical composition, comprising:
an immunologically effective amount of a virus of claim 8; and
a pharmaceutically acceptable carrier, excipient, adjuvant or diluent.

* * * * *

SEQUENCE LISTING

```
<160> NUMBER OF SEQ ID NOS: 25

<210> SEQ ID NO 1
<211> LENGTH: 104
<212> TYPE: PRT
<213> ORGANISM: Porcine Circovirus
<220> FEATURE:
<223> OTHER INFORMATION: Type 2

<400> SEQUENCE: 1

Met Val Thr Ile Pro Pro Leu Val Ser Arg Trp Phe Pro Val Cys Gly
 1               5                  10                  15

Phe Arg Val Cys Lys Ile Ser Ser Pro Phe Ala Phe Thr Thr Thr Arg
                20                  25                  30

Trp Pro His Asn Asp Val Tyr Ile Arg Leu Pro Ile Thr Leu Leu His
            35                  40                  45

Phe Pro Ala His Phe Gln Lys Phe Ser Gln Pro Ala Glu Ile Ser Asp
        50                  55                  60

Lys Arg Tyr Arg Val Leu Leu Cys Asn Gly His Gln Thr Pro Ala Leu
    65                  70                  75                  80

Gln Gln Gly Thr His Ser Ser Arg Gln Val Thr Pro Leu Ser Leu Arg
                85                  90                  95

Ser Arg Ser Ser Thr Phe Tyr Gln
               100
```

<210> SEQ ID NO 2
<211> LENGTH: 315
<212> TYPE: DNA
<213> ORGANISM: Porcine Circovirus
<220> FEATURE:
<223> OTHER INFORMATION: Type 2

<400> SEQUENCE: 2

| | | | | | |
|---|---|---|---|---|---|
| atggtaacca | tcccaccact | tgtttctagg | tggtttccag | tatgtggttt | ccgggtctgc | 60 |
| aaaattagca | gcccatttgc | ttttaccaca | accaggtggc | cccacaatga | cgtgtacatt | 120 |
| cgtcttccaa | tcacgcttct | gcattttccc | gctcactttc | aaaagttcag | ccagcccgcg | 180 |
| gaaatttctg | acaaacgtta | cagggtgctg | ctctgcaacg | gtcaccagac | tcccgctctc | 240 |
| caacaaggta | ctcacagcag | tagacaggtc | actccgttgt | ccttgagatc | taggagctcc | 300 |
| acattctatc | agtaa | | | | | 315 |

<210> SEQ ID NO 3
<211> LENGTH: 315
<212> TYPE: DNA
<213> ORGANISM: Porcine Circovirus
<220> FEATURE:
<223> OTHER INFORMATION: Type 2

<400> SEQUENCE: 3

| | | | | | |
|---|---|---|---|---|---|
| gtggtaacca | tcccaccact | tgtttctagg | tggtttccag | tatgtggttt | ccgggtctgc | 60 |
| aaaattagca | gcccatttgc | ttttaccaca | accaggtggc | cccacaatga | cgtgtacatt | 120 |
| cgtcttccaa | tcacgcttct | gcattttccc | gctcactttc | aaaagttcag | ccagcccgcg | 180 |
| gaaatttctg | acaaacgtta | cagggtgctg | ctctgcaacg | gtcaccagac | tcccgctctc | 240 |
| caacaaggta | ctcacagcag | tagacaggtc | actccgttgt | ccttgagatc | taggagctcc | 300 |
| acattctatc | agtaa | | | | | 315 |

<210> SEQ ID NO 4
<211> LENGTH: 1767
<212> TYPE: DNA
<213> ORGANISM: Porcine Circovirus
<220> FEATURE:
<223> OTHER INFORMATION: Type 2

<400> SEQUENCE: 4

| | | | | | |
|---|---|---|---|---|---|
| accagcgcac | ttcggcagcg | gcagcacctc | ggcagcacct | cagcagcaac | atgcccagca | 60 |
| agaagaatgg | aagaagcgga | ccccaaccac | acaaaaggtg | ggtgttcacg | ctgaataatc | 120 |
| cttccgaaga | cgagcgcaag | aaaatacggg | agcttccaat | ctccctttt | gattatttta | 180 |
| ttgttggcga | ggagggtaat | gaggaaggac | gaacaccca | cctccagggg | ttcgctaatt | 240 |
| ttgtgaagaa | gcaaacattt | aataaagtga | atggtatttt | cggtgcccgc | tgccacatcg | 300 |
| agaaagcgaa | aggaactgat | cagcagaata | aagaatactg | cagtaaagaa | ggcaacttac | 360 |
| tgatagaatg | tggagctcct | agatctcaag | acaacggag | tgacctgtct | actgctgtga | 420 |
| gtaccttgtt | ggagagcggg | agtctggtga | ccgttgcaga | gcagcaccct | gtaacgtttg | 480 |
| tcagaaattt | ccgcgggctg | gctgaacttt | tgaaagtgag | cggaaaaatg | cagaagcgtg | 540 |
| attggaagac | gaatgtacac | gtcattgtgg | ggccacctgg | ttgtggtaaa | agcaaatggg | 600 |
| ctgctaattt | tgcagacccg | gaaaccacat | actggaaacc | acctagaaac | aagtggtggg | 660 |
| atggttacca | tggtgaagaa | gtggttgtta | ttgatgactt | ttatggctgg | ctgccctggg | 720 |
| atgatctact | gagactgtgt | gatcgatatc | cattgactgt | agagactaaa | ggtggaactg | 780 |

```
tacctttttt ggcccgcagt attctgatta ccagcaatca gaccccgttg aatggtact      840 cctcaactgc tgtcccagct gtagaagctc tttatcggag gattacttcc ttggtatttt    900
ggaagaatgc tacagaacaa tccacggagg aagggggcca gttcgtcacc ctttcccccc    960
catgccctga atttccatat gaataaaatt actgagtctt ttttatcact tcgtaatggt   1020
ttttattatt tattaagggt taagtggggg gtctttaaga ttaaattctc tgaattgtac   1080
atacatggtt acacggatat tgtattcctg gtcgtatata ctgttttcga acgcagtgcc   1140
gaggcctacg tggtctacat ttccagcagt ttgtagtctc agccacagct gatttctttt   1200
gttgtttggt tggaagtaat caatagtgga atctaggaca ggtttggggg taaagtagcg   1260
ggagtggtag gagaagggct gggttatggt atggcgggag gagtagttta catagggtc    1320 ataggtgagg gctgtggcct ttgttacaaa gttatcatct agaataacag cactggagcc   1380
cactcccctg tcaccctggg tgatcgggga gcagggccag aattcaacct taaccttttct  1440 tattctgtag tattcaaagg gcacagaagc ggggtttga gccccctcct ggggaagaa     1500 aatcattaat attgaatcta tcatgtccac cgcccaagag ggcgttttga ctgtggttcg   1560
cttgatagta tatccgaagg tgcgggagag gcgggtgttg aagatgccat ttttccttct   1620
ccagcggtaa cggtggcggg ggtggacgag ccaggggcgg cggcggagga tctggccaag   1680
atggctgcgg gggcggtgtc ttcttctccg gtaacgcctc cttggatacg tcatatctga   1740
aaacgaaaga agtgcgctgt aagtatt                                        1767

<210> SEQ ID NO 5
<211> LENGTH: 30
<212> TYPE: DNA
<213> ORGANISM: Porcine Circovirus
<220> FEATURE:
<223> OTHER INFORMATION: Type 2

<400> SEQUENCE: 5
gggatggtta ccacggtgaa gtggttgtta                                      30

<210> SEQ ID NO 6
<211> LENGTH: 33
<212> TYPE: DNA
<213> ORGANISM: Porcine Circovirus
<220> FEATURE:
<223> OTHER INFORMATION: Type 2

<400> SEQUENCE: 6
taacaaccac ttcttcaccg tggtaaccat ccc                                  33

<210> SEQ ID NO 7
<211> LENGTH: 27
<212> TYPE: DNA
<213> ORGANISM: Porcine Circovirus
<220> FEATURE:
<223> OTHER INFORMATION: Type 2

<400> SEQUENCE: 7
tgcactgcag taaagaaggc aacttac                                         27

<210> SEQ ID NO 8
<211> LENGTH: 27
<212> TYPE: DNA
<213> ORGANISM: Porcine Circovirus
<220> FEATURE:
<223> OTHER INFORMATION: Type 2
```

```
<400> SEQUENCE: 8
tgcactgcag tattctttat tctgctg                                        27

<210> SEQ ID NO 9
<211> LENGTH: 31
<212> TYPE: DNA
<213> ORGANISM: Porcine Circovirus
<220> FEATURE:
<223> OTHER INFORMATION: Type 2

<400> SEQUENCE: 9
ccgctcgagc tatgcccagc aagaagaatg g                                   31

<210> SEQ ID NO 10
<211> LENGTH: 29
<212> TYPE: DNA
<213> ORGANISM: Porcine Circovirus
<220> FEATURE:
<223> OTHER INFORMATION: Type 2

<400> SEQUENCE: 10
cggggtacct cagtaattta tttcatatg                                      29

<210> SEQ ID NO 11
<211> LENGTH: 31
<212> TYPE: DNA
<213> ORGANISM: Porcine Circovirus
<220> FEATURE:
<223> OTHER INFORMATION: Type 2

<400> SEQUENCE: 11
cccaagcttc gatgacgtac ccaaggaggc g                                   31

<210> SEQ ID NO 12
<211> LENGTH: 30
<212> TYPE: DNA
<213> ORGANISM: Porcine Circovirus
<220> FEATURE:
<223> OTHER INFORMATION: Type 2

<400> SEQUENCE: 12
cggggtacct tatggtttaa gtgggggtc                                      30

<210> SEQ ID NO 13
<211> LENGTH: 33
<212> TYPE: DNA
<213> ORGANISM: Porcine Circovirus
<220> FEATURE:
<223> OTHER INFORMATION: Type 2

<400> SEQUENCE: 13
cccaagcttc gatggtaacc atcccaccac ttg                                 33

<210> SEQ ID NO 14
<211> LENGTH: 31
<212> TYPE: DNA
<213> ORGANISM: Porcine Circovirus
<220> FEATURE:
<223> OTHER INFORMATION: Type 2

<400> SEQUENCE: 14
cggggtacct tacttatcga gtgtggagct c                                   31

<210> SEQ ID NO 15
<211> LENGTH: 22
```

```
<212> TYPE: DNA
<213> ORGANISM: Porcine Circovirus
<220> FEATURE:
<223> OTHER INFORMATION: Type 2

<400> SEQUENCE: 15
atggtaacca tcccaccact tg                                          22

<210> SEQ ID NO 16
<211> LENGTH: 20
<212> TYPE: DNA
<213> ORGANISM: Porcine Circovirus
<220> FEATURE:
<223> OTHER INFORMATION: Type 2

<400> SEQUENCE: 16
ttactgatag aatgtggagc                                             20

<210> SEQ ID NO 17
<211> LENGTH: 39
<212> TYPE: DNA
<213> ORGANISM: Porcine Circovirus
<220> FEATURE:
<223> OTHER INFORMATION: Type 2

<400> SEQUENCE: 17
atggtaacca tcccaccatt gtttctaggt ggtttccag                        39

<210> SEQ ID NO 18
<211> LENGTH: 40
<212> TYPE: DNA
<213> ORGANISM: Porcine Circovirus
<220> FEATURE:
<223> OTHER INFORMATION: Type 2

<400> SEQUENCE: 18
taatacgact cactataggt cagaaatttc cgcgggctgg                       40

<210> SEQ ID NO 19
<211> LENGTH: 315
<212> TYPE: DNA
<213> ORGANISM: Porcine Circovirus
<220> FEATURE:
<223> OTHER INFORMATION: Type 2

<400> SEQUENCE: 19
atggtaacca tcccaccact tgtttctagg tggtttccag tatgtggttt ccgggtctgc    60
aaaattagca gcccattttg atttaccaca accaggtggc cccacaatga cgtgtacatt   120
cgtcttccaa tcacgcttct gcattttccc gctcactttc aaaagttcag ccagcccgcg   180
gaaatttctg acaaacgtta cagggtgctg ctctgcaacg gtcaccagac tcccgctctc   240
caacaaggta ctcacagcag tagacaggtc actccgttgt ccttgagatc taggagctcc   300
acattctatc agtaa                                                   315

<210> SEQ ID NO 20
<211> LENGTH: 315
<212> TYPE: DNA
<213> ORGANISM: Porcine Circovirus
<220> FEATURE:
<223> OTHER INFORMATION: Type 2

<400> SEQUENCE: 20
atggtaacca tcccaccact tgtttctagg tggtttccag tatgtggttt ccgggtctgc    60
```

-continued

| | |
|---|---|
| aaaattagca gcccatttgc ttttaccaca accaggtggc cccacaatga cgtgtacatt | 120 |
| cgtcttccaa tcacgcttct gcattttccc gctgactttc aaaagttcag ccagcccgcg | 180 |
| gaaatttctg acaaacgtta cagggtgctg ctctgcaacg gtcaccagac tcccgctctc | 240 |
| caacaaggta ctcacagcag tagacaggtc actccgttgt ccttgagatc taggagctcc | 300 |
| acattctatc agtaa | 315 |

<210> SEQ ID NO 21
<211> LENGTH: 315
<212> TYPE: DNA
<213> ORGANISM: Porcine Circovirus
<220> FEATURE:
<223> OTHER INFORMATION: Type 2

<400> SEQUENCE: 21

| | |
|---|---|
| atggtaacca tcccaccact tgtttctagg tggtttccag tatgtggttt ccgggtctgc | 60 |
| aaaattagca gcccatttgc ttttaccaca accaggtggc cccacaatga cgtgtacatt | 120 |
| cgtcttccaa tcacgcttct gcattttccc gctcactttc aaaagttcag ccagcccgcg | 180 |
| aaaatttctg acaaacgtta cagggtgctg ctctgcaacg gtcaccagac tcccgctctc | 240 |
| caacaaggta ctcacagcag tagacaggtc actccgttgt ccttgagatc taggagctcc | 300 |
| acattctatc agtaa | 315 |

<210> SEQ ID NO 22
<211> LENGTH: 315
<212> TYPE: DNA
<213> ORGANISM: Porcine Circovirus
<220> FEATURE:
<223> OTHER INFORMATION: Type 2

<400> SEQUENCE: 22

| | |
|---|---|
| atggtaacca tcccaccact tgtttctagg tggtttccag tatgtggttt ccgggtctgc | 60 |
| aaaattagca gcccatttgc ttttaccaca accaggtggc cccacaatga cgtgtacatt | 120 |
| cgtcttccaa tcacgcttct gcattttccc gctcactttc aaaagttcag ccagcccgcg | 180 |
| gaaatttctg acaaacgtta cagggtgctg ctctgcaacg gtcaccagac tcccgctctc | 240 |
| caacaaggta cttacagcag tagacaggtc actccgttgt ccttgagatc taggagctcc | 300 |
| acattctatc agtaa | 315 |

<210> SEQ ID NO 23
<211> LENGTH: 315
<212> TYPE: DNA
<213> ORGANISM: Porcine Circovirus
<220> FEATURE:
<223> OTHER INFORMATION: Type 2

<400> SEQUENCE: 23

| | |
|---|---|
| gtggtaacca tcccaccact tgtttctagg tggtttccag tatgtggttt ccgggtctgc | 60 |
| aaaattagca gcccattttg atttaccaca accaggtggc cccacaatga cgtgtacatt | 120 |
| cgtcttccaa tcacgcttct gcattttccc gctcactttc aaaagttcag ccagcccgcg | 180 |
| gaaatttctg acaaacgtta cagggtgctg ctctgcaacg gtcaccagac tcccgctctc | 240 |
| caacaaggta ctcacagcag tagacaggtc actccgttgt ccttgagatc taggagctcc | 300 |
| acattctatc agtaa | 315 |

<210> SEQ ID NO 24
<211> LENGTH: 315

```
<212> TYPE: DNA
<213> ORGANISM: Porcine Circovirus
<220> FEATURE:
<223> OTHER INFORMATION: Type 2

<400> SEQUENCE: 24
gtggtaacca tcccaccact tgtttctagg tggtttccag tatgtggttt ccgggtctgc      60
aaaattagca gcccatttgc ttttaccaca accaggtggc cccacaatga cgtgtacatt     120
cgtcttccaa tcacgcttct gcattttccc gctcactttc aaaagttcag ccagcccgcg     180
aaaatttctg acaaacgtta cagggtgctg ctctgcaacg gtcaccagac tcccgctctc     240
caacaaggta ctcacagcag tagacaggtc actccgttgt ccttgagatc taggagctcc     300
acattctatc agtaa                                                      315

<210> SEQ ID NO 25
<211> LENGTH: 315
<212> TYPE: DNA
<213> ORGANISM: Porcine Circovirus
<220> FEATURE:
<223> OTHER INFORMATION: Type 2

<400> SEQUENCE: 25
gtggtaacca tcccaccact tgtttctagg tggtttccag tatgtggttt ccgggtctgc      60
aaaattagca gcccattttg atttaccaca accaggtggc cccacaatga cgtgtacatt     120
cgtcttccaa tcacgcttct gcattttccc gctcactttc aaaagttcag ccagcccgcg     180
aaaatttctg acaaacgtta cagggtgctg ctctgcaacg gtcaccagac tcccgctctc     240
caacaaggta ctcacagcag tagacaggtc actccgttgt ccttgagatc taggagctcc     300
acattctatc agtaa                                                      315
```